US012797070B2

(12) United States Patent
May et al.

(10) Patent No.: US 12,797,070 B2
(45) Date of Patent: Nov. 17, 2026

(54) SURGICAL STAPLER WITH ROTATABLE LOCKOUT COLLAR

(71) Applicant: Cilag GmbH International, Zug (CH)

(72) Inventors: John P. May, Mason, OH (US); Shannon L. Jones, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/883,569

(22) Filed: Sep. 12, 2024

(65) Prior Publication Data

US 2026/0069270 A1 Mar. 12, 2026

(51) Int. Cl.
*A61B 17/072* (2006.01)

(52) U.S. Cl.
CPC .................... *A61B 17/07207* (2013.01); *A61B 2017/07271* (2013.01); *A61B 2017/07285* (2013.01)

(58) Field of Classification Search
CPC ............ A61B 17/072; A61B 17/07207; A61B 17/285; A61B 17/295; A61B 2017/07271; A61B 2017/07278; A61B 2017/07285
USPC ................................ 227/175.2, 175.3, 175.4
See application file for complete search history.

(56) References Cited

U.S. PATENT DOCUMENTS

| | | | |
|---|---|---|---|
| 3,826,978 | A | 7/1974 | Kelly |
| 4,805,823 | A | 2/1989 | Rothfuss |
| 4,892,244 | A | 1/1990 | Fox et al. |
| 5,129,570 | A | 7/1992 | Schulze et al. |
| 5,219,111 | A | 6/1993 | Bilotti et al. |
| 5,397,046 | A | 3/1995 | Savage et al. |
| 5,403,312 | A | 4/1995 | Yates et al. |
| 5,415,334 | A | 5/1995 | Williamson et al. |
| 5,465,895 | A | 11/1995 | Knodel et al. |
| 5,485,947 | A | 1/1996 | Olson et al. |
| 5,584,425 | A | 12/1996 | Savage et al. |
| 5,597,107 | A | 1/1997 | Knodel et al. |

(Continued)

FOREIGN PATENT DOCUMENTS

| | | | | |
|---|---|---|---|---|
| CN | 202982103 U | | 6/2013 | |
| CN | 103860222 A | | 6/2014 | |
| EP | 3123952 A1 | * | 2/2017 | ....... A61B 17/07207 |

OTHER PUBLICATIONS

European Search Report and Written Opinion dated Feb. 14, 2024, for Application No. 23196507.0, 12 pages.

(Continued)

*Primary Examiner* — Linda J. Hodge
(74) *Attorney, Agent, or Firm* — FBT Gibbons LLP

(57) ABSTRACT

An apparatus including a first jaw to selectively receive a staple cartridge and define a longitudinal jaw axis. The apparatus further includes a second jaw. The first and second jaws being able to cooperate to clamp and staple tissue. The apparatus further including a knife to actuate relative to the first jaw and the second jaw along the longitudinal jaw axis while the staple cartridge is housed within the first jaw to thereby cut and staple tissue clamped by the first and second jaws. The knife defines a longitudinal knife axis that extends along the longitudinal jaw axis. The apparatus further includes a lock rotatable relative to the knife about the longitudinal knife axis between an unlocked configuration and a locked configuration. The lock being able to inhibit distal actuation of the knife in the locked configuration and permit distal actuation of the knife in the unlocked configuration.

19 Claims, 25 Drawing Sheets

(56) References Cited

U.S. PATENT DOCUMENTS

| | | | |
|---|---|---|---|
| 5,632,432 | A | 5/1997 | Schulze et al. |
| 5,669,544 | A | 9/1997 | Schulze et al. |
| 5,673,840 | A | 10/1997 | Schulze et al. |
| 5,673,841 | A | 10/1997 | Schulze et al. |
| 5,692,668 | A | 12/1997 | Schulze et al. |
| 5,704,534 | A | 1/1998 | Huitema et al. |
| 5,709,334 | A | 1/1998 | Sorrentino et al. |
| 5,779,130 | A | 7/1998 | Alesi et al. |
| 5,782,396 | A | 7/1998 | Mastri et al. |
| 5,785,232 | A | 7/1998 | Vidal et al. |
| 5,792,135 | A | 8/1998 | Madhani et al. |
| 5,814,055 | A | 9/1998 | Knodel et al. |
| 5,817,084 | A | 10/1998 | Jensen |
| 5,878,193 | A | 3/1999 | Wang et al. |
| 5,878,938 | A | 3/1999 | Bittner et al. |
| 5,954,259 | A | 9/1999 | Viola et al. |
| 6,063,098 | A | 5/2000 | Houser et al. |
| 6,079,606 | A | 6/2000 | Milliman et al. |
| 6,109,500 | A | 8/2000 | Alli et al. |
| 6,231,565 | B1 | 5/2001 | Tovey et al. |
| 6,364,888 | B1 | 4/2002 | Niemeyer et al. |
| 6,439,446 | B1 | 8/2002 | Perry et al. |
| 6,440,146 | B2 | 8/2002 | Nicholas et al. |
| 6,488,196 | B1 | 12/2002 | Fenton, Jr. |
| 6,722,552 | B2 | 4/2004 | Fenton, Jr. |
| 6,783,524 | B2 | 8/2004 | Anderson et al. |
| 6,835,199 | B2 | 12/2004 | McGuckin, Jr. et al. |
| 6,978,921 | B2 | 12/2005 | Shelton, IV et al. |
| 6,988,649 | B2 | 1/2006 | Shelton, IV et al. |
| 7,000,818 | B2 | 2/2006 | Shelton, IV et al. |
| 7,044,352 | B2 | 5/2006 | Shelton, IV et al. |
| 7,143,923 | B2 | 12/2006 | Shelton, IV et al. |
| 7,303,108 | B2 | 12/2007 | Shelton, IV |
| 7,328,828 | B2 | 2/2008 | Ortiz et al. |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,422,139 | B2 | 9/2008 | Shelton, IV et al. |
| 7,434,715 | B2 | 10/2008 | Shelton, IV et al. |
| 7,461,767 | B2 | 12/2008 | Viola et al. |
| 7,464,849 | B2 | 12/2008 | Shelton, IV et al. |
| 7,510,107 | B2 | 3/2009 | Timm et al. |
| 7,524,320 | B2 | 4/2009 | Tierney et al. |
| 7,568,603 | B2 | 8/2009 | Shelton, IV et al. |
| 7,588,177 | B2 | 9/2009 | Racenet |
| 7,617,961 | B2 | 11/2009 | Viola |
| 7,641,095 | B2 | 1/2010 | Viola |
| 7,644,848 | B2 | 1/2010 | Swayze et al. |
| 7,670,334 | B2 | 3/2010 | Hueil et al. |
| 7,691,098 | B2 | 4/2010 | Wallace et al. |
| 7,695,485 | B2 | 4/2010 | Whitman et al. |
| 7,721,930 | B2 | 5/2010 | McKenna et al. |
| 7,721,936 | B2 | 5/2010 | Shalton, IV et al. |
| 7,753,245 | B2 | 7/2010 | Boudreaux et al. |
| 7,780,055 | B2 | 8/2010 | Scirica et al. |
| 7,806,891 | B2 | 10/2010 | Nowlin et al. |
| 7,810,692 | B2 | 10/2010 | Hall et al. |
| 7,832,408 | B2 | 11/2010 | Shelton, IV et al. |
| 7,845,537 | B2 | 12/2010 | Shelton, IV et al. |
| 7,955,347 | B2 | 6/2011 | Stout |
| 7,959,051 | B2 | 6/2011 | Smith et al. |
| 7,963,433 | B2 | 6/2011 | Whitman et al. |
| 7,980,443 | B2 | 7/2011 | Scheib et al. |
| 8,020,743 | B2 | 9/2011 | Shelton, IV |
| 8,083,119 | B2 | 12/2011 | Prommersberger |
| 8,083,120 | B2 | 12/2011 | Shelton, IV et al. |
| 8,210,411 | B2 | 7/2012 | Yates et al. |
| 8,220,688 | B2 | 7/2012 | Laurent et al. |
| 8,241,322 | B2 | 8/2012 | Whitman et al. |
| 8,308,040 | B2 | 11/2012 | Huang et al. |
| 8,360,297 | B2 | 1/2013 | Shelton, IV et al. |
| 8,393,514 | B2 | 3/2013 | Shelton, IV et al. |
| 8,408,439 | B2 | 4/2013 | Huang et al. |
| 8,453,914 | B2 | 6/2013 | Laurent et al. |
| 8,459,520 | B2 | 6/2013 | Giordano et al. |
| 8,469,254 | B2 | 6/2013 | Czernik et al. |
| 8,479,969 | B2 | 7/2013 | Shelton, IV |
| 8,561,870 | B2 | 10/2013 | Baxter, III et al. |
| 8,573,461 | B2 | 11/2013 | Shelton, IV et al. |
| 8,573,465 | B2 | 11/2013 | Shelton, IV |
| 8,584,921 | B2 | 11/2013 | Scirica |
| 8,602,288 | B2 | 12/2013 | Shelton, IV et al. |
| 8,608,045 | B2 | 12/2013 | Smith et al. |
| 8,616,431 | B2 | 12/2013 | Timm et al. |
| 8,632,535 | B2 | 1/2014 | Shelton, IV et al. |
| 8,708,213 | B2 | 4/2014 | Shelton, IV et al. |
| 8,733,613 | B2 | 5/2014 | Huitema et al. |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,822,934 | B2 | 9/2014 | Sayeh et al. |
| 8,844,789 | B2 | 9/2014 | Shelton, IV et al. |
| 8,876,857 | B2 | 11/2014 | Burbank |
| 8,989,903 | B2 | 3/2015 | Weir et al. |
| 9,023,069 | B2 | 5/2015 | Kasvikis et al. |
| 9,060,770 | B2 | 6/2015 | Shelton, IV et al. |
| 9,072,535 | B2 | 7/2015 | Shelton, IV |
| 9,078,653 | B2 | 7/2015 | Leimbach et al. |
| 9,101,358 | B2 | 8/2015 | Kerr et al. |
| 9,186,142 | B2 | 11/2015 | Fanelli et al. |
| 9,274,095 | B2 | 3/2016 | Humayun et al. |
| 9,289,211 | B2 | 3/2016 | Williams et al. |
| 9,307,986 | B2 | 4/2016 | Hall et al. |
| 9,326,767 | B2 | 5/2016 | Koch, Jr. et al. |
| 9,332,987 | B2 | 5/2016 | Leimbach et al. |
| 9,345,481 | B2 | 5/2016 | Hall et al. |
| 9,351,726 | B2 | 5/2016 | Leimbach et al. |
| 9,351,727 | B2 | 5/2016 | Leimbach et al. |
| 9,358,003 | B2 | 6/2016 | Hall et al. |
| 9,386,984 | B2 | 7/2016 | Aronhalt et al. |
| 9,398,911 | B2 | 7/2016 | Auld |
| 9,421,062 | B2 | 8/2016 | Houser et al. |
| 9,468,438 | B2 | 10/2016 | Baber et al. |
| 9,517,065 | B2 | 12/2016 | Simms et al. |
| 9,526,499 | B2 | 12/2016 | Kostrzewski et al. |
| 9,554,794 | B2 | 1/2017 | Baber et al. |
| 9,622,746 | B2 | 4/2017 | Simms et al. |
| 9,629,623 | B2 | 4/2017 | Lytle, IV et al. |
| 9,629,629 | B2 | 4/2017 | Leimbach et al. |
| 9,649,110 | B2 | 5/2017 | Parihar et al. |
| 9,687,230 | B2 | 6/2017 | Leimbach et al. |
| 9,690,362 | B2 | 6/2017 | Leimbach et al. |
| 9,700,309 | B2 | 7/2017 | Jaworek et al. |
| 9,717,497 | B2 | 8/2017 | Zerkle et al. |
| 9,717,498 | B2 | 8/2017 | Aranyi et al. |
| 9,724,094 | B2 | 8/2017 | Baber et al. |
| 9,733,663 | B2 | 8/2017 | Leimbach et al. |
| 9,737,301 | B2 | 8/2017 | Baber et al. |
| 9,737,303 | B2 | 8/2017 | Shelton, IV et al. |
| 9,743,929 | B2 | 8/2017 | Leimbach et al. |
| 9,750,499 | B2 | 9/2017 | Leimbach et al. |
| 9,757,126 | B2 | 9/2017 | Cappola |
| 9,757,128 | B2 | 9/2017 | Baber et al. |
| 9,782,169 | B2 | 10/2017 | Kimsey et al. |
| 9,788,836 | B2 | 10/2017 | Overmyer et al. |
| 9,795,379 | B2 | 10/2017 | Leimbach et al. |
| 9,801,626 | B2 | 10/2017 | Parihar et al. |
| 9,804,618 | B2 | 10/2017 | Leimbach et al. |
| 9,808,244 | B2 | 11/2017 | Leimbach et al. |
| 9,808,245 | B2 | 11/2017 | Shelton, IV et al. |
| 9,808,248 | B2 | 11/2017 | Hoffman |
| 9,814,460 | B2 | 11/2017 | Kimsey et al. |
| 9,820,738 | B2 | 11/2017 | Lytle, IV et al. |
| 9,820,741 | B2 | 11/2017 | Kostrzewski |
| 9,826,976 | B2 | 11/2017 | Parihar et al. |
| 9,826,977 | B2 | 11/2017 | Leimbach et al. |
| 9,826,978 | B2 | 11/2017 | Shelton, IV et al. |
| 9,839,487 | B2 | 12/2017 | Dachs, II |
| 9,844,368 | B2 | 12/2017 | Boudreaux et al. |
| 9,844,374 | B2 | 12/2017 | Lytle, IV et al. |
| 9,844,375 | B2 | 12/2017 | Overmyer et al. |
| 9,861,363 | B2 | 1/2018 | Chen et al. |
| 9,867,612 | B2 | 1/2018 | Parihar et al. |

(56) References Cited

U.S. PATENT DOCUMENTS

| | | | |
|---|---|---|---|
| 9,883,860 | B2 | 2/2018 | Leimbach et al. |
| 9,888,919 | B2 | 2/2018 | Leimbach et al. |
| 9,895,148 | B2 | 2/2018 | Shelton, IV et al. |
| 9,901,342 | B2 | 2/2018 | Shelton, IV et al. |
| 9,913,642 | B2 | 3/2018 | Leimbach et al. |
| 9,924,961 | B2 | 3/2018 | Shelton, IV et al. |
| 9,931,118 | B2 | 4/2018 | Shelton, IV et al. |
| 9,931,120 | B2 | 4/2018 | Chen et al. |
| 9,943,309 | B2 | 4/2018 | Shelton, IV et al. |
| 9,968,355 | B2 | 5/2018 | Shelton, IV et al. |
| 9,987,000 | B2 | 6/2018 | Shelton, IV et al. |
| 9,993,248 | B2 | 6/2018 | Shelton, IV et al. |
| 9,993,258 | B2 | 6/2018 | Shelton, IV et al. |
| 10,004,497 | B2 | 6/2018 | Overmyer et al. |
| 10,004,498 | B2 | 6/2018 | Morgan et al. |
| 10,004,501 | B2 | 6/2018 | Shelton, IV et al. |
| D822,206 | S | 7/2018 | Shelton, IV et al. |
| 10,011,018 | B2 | 7/2018 | McGrogan et al. |
| 10,013,049 | B2 | 7/2018 | Leimbach et al. |
| 10,016,199 | B2 | 7/2018 | Baber et al. |
| 10,028,761 | B2 | 7/2018 | Leimbach et al. |
| D826,405 | S | 8/2018 | Shelton, IV et al. |
| 10,045,776 | B2 | 8/2018 | Shelton, IV et al. |
| 10,045,779 | B2 | 8/2018 | Savage et al. |
| 10,045,782 | B2 | 8/2018 | Murthy Aravalli |
| 10,052,044 | B2 | 8/2018 | Shelton, IV et al. |
| 10,052,102 | B2 | 8/2018 | Baxter, III et al. |
| 10,064,620 | B2 | 9/2018 | Gettinger et al. |
| 10,064,622 | B2 | 9/2018 | Murthy Aravalli |
| 10,071,452 | B2 | 9/2018 | Shelton, IV et al. |
| 10,085,748 | B2 | 10/2018 | Morgan et al. |
| 10,085,811 | B2 | 10/2018 | Weir et al. |
| 10,092,292 | B2 | 10/2018 | Boudreaux et al. |
| 10,111,679 | B2 | 10/2018 | Baber et al. |
| 10,117,649 | B2 | 11/2018 | Baxter, III et al. |
| 10,130,359 | B2 | 11/2018 | Hess et al. |
| 10,130,360 | B2 | 11/2018 | Olson et al. |
| 10,130,367 | B2 | 11/2018 | Cappola et al. |
| 10,135,242 | B2 | 11/2018 | Baber et al. |
| 10,136,887 | B2 | 11/2018 | Shelton, IV et al. |
| 10,149,680 | B2 | 12/2018 | Parihar et al. |
| 10,154,841 | B2 | 12/2018 | Weaner et al. |
| 10,159,483 | B2 | 12/2018 | Beckman et al. |
| 10,172,669 | B2 | 1/2019 | Felder et al. |
| 10,175,127 | B2 | 1/2019 | Collins et al. |
| 10,176,992 | B2 | 1/2019 | Wise et al. |
| 10,180,463 | B2 | 1/2019 | Beckman et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |
| 10,188,385 | B2 | 1/2019 | Kerr et al. |
| 10,201,364 | B2 | 2/2019 | Leimbach et al. |
| 10,226,250 | B2 | 3/2019 | Beckman et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,033 | B2 | 4/2019 | Overmyer et al. |
| 10,245,036 | B1 | 4/2019 | Schaller |
| 10,245,038 | B2 | 4/2019 | Hopkins et al. |
| 10,258,331 | B2 | 4/2019 | Shelton, IV et al. |
| 10,265,068 | B2 | 4/2019 | Harris et al. |
| 10,271,847 | B2 | 4/2019 | Racenet et al. |
| 10,271,851 | B2 | 4/2019 | Shelton, IV et al. |
| D847,989 | S | 5/2019 | Shelton, IV et al. |
| 10,285,705 | B2 | 5/2019 | Shelton, IV et al. |
| 10,292,701 | B2 | 5/2019 | Scheib et al. |
| 10,292,704 | B2 | 5/2019 | Harris et al. |
| 10,303,641 | B2 | 5/2019 | Collins et al. |
| D850,617 | S | 6/2019 | Shelton, IV et al. |
| D851,762 | S | 6/2019 | Shelton, IV et al. |
| 10,307,159 | B2 | 6/2019 | Harris et al. |
| 10,307,170 | B2 | 6/2019 | Parfett et al. |
| 10,314,577 | B2 | 6/2019 | Laurent et al. |
| 10,314,582 | B2 | 6/2019 | Shelton, IV et al. |
| 10,321,907 | B2 | 6/2019 | Shelton, IV et al. |
| D854,151 | S | 7/2019 | Shelton, IV et al. |
| 10,335,147 | B2 | 7/2019 | Rector et al. |
| 10,335,149 | B2 | 7/2019 | Baxter, III et al. |
| 10,342,543 | B2 | 7/2019 | Shelton, IV et al. |
| 10,350,016 | B2 | 7/2019 | Burbank et al. |
| 10,357,246 | B2 | 7/2019 | Shelton, IV et al. |
| 10,363,037 | B2 | 7/2019 | Aronhalt et al. |
| 10,368,861 | B2 | 8/2019 | Baxter, III et al. |
| 10,368,865 | B2 | 8/2019 | Harris et al. |
| 10,368,867 | B2 | 8/2019 | Harris et al. |
| 10,376,263 | B2 | 8/2019 | Morgan et al. |
| 10,390,897 | B2 | 8/2019 | Kostrzewski |
| 10,405,857 | B2 | 9/2019 | Shelton, IV et al. |
| 10,405,863 | B2 | 9/2019 | Wise et al. |
| 10,413,291 | B2 | 9/2019 | Worthington et al. |
| 10,413,293 | B2 | 9/2019 | Shelton, IV et al. |
| 10,413,297 | B2 | 9/2019 | Harris et al. |
| 10,418,441 | B2 | 9/2019 | Naito |
| 10,420,552 | B2 | 9/2019 | Shelton, IV et al. |
| 10,426,471 | B2 | 10/2019 | Shelton, IV et al. |
| 10,433,837 | B2 | 10/2019 | Worthington et al. |
| 10,433,849 | B2 | 10/2019 | Shelton, IV et al. |
| 10,441,279 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,456,132 | B2 | 10/2019 | Gettinger et al. |
| 10,456,140 | B2 | 10/2019 | Shelton, IV et al. |
| 10,470,762 | B2 | 11/2019 | Leimbach et al. |
| 10,470,764 | B2 | 11/2019 | Baxter, III et al. |
| 10,478,181 | B2 | 11/2019 | Shelton, IV et al. |
| 10,478,190 | B2 | 11/2019 | Miller et al. |
| 10,485,542 | B2 | 11/2019 | Shelton, IV et al. |
| 10,485,543 | B2 | 11/2019 | Shelton, IV et al. |
| 10,485,621 | B2 | 11/2019 | Morrissette et al. |
| D869,655 | S | 12/2019 | Shelton, IV et al. |
| 10,492,785 | B2 | 12/2019 | Overmyer et al. |
| 10,499,914 | B2 | 12/2019 | Huang et al. |
| 10,517,595 | B2 | 12/2019 | Hunter et al. |
| 10,517,596 | B2 | 12/2019 | Hunter et al. |
| 10,524,789 | B2 | 1/2020 | Swayze et al. |
| 10,531,874 | B2 | 1/2020 | Morgan et al. |
| 10,537,324 | B2 | 1/2020 | Shelton, IV et al. |
| 10,537,325 | B2 | 1/2020 | Bakos et al. |
| 10,537,400 | B2 | 1/2020 | Dachs, II et al. |
| 10,542,979 | B2 | 1/2020 | Shelton, IV et al. |
| 10,542,982 | B2 | 1/2020 | Beckman et al. |
| 10,542,991 | B2 | 1/2020 | Shelton, IV et al. |
| 10,543,051 | B2 | 1/2020 | Schena et al. |
| 10,548,504 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,632 | B2 | 2/2020 | Miller et al. |
| 10,582,928 | B2 | 3/2020 | Hunter et al. |
| 10,588,625 | B2 | 3/2020 | Weaner et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,603,036 | B2 | 3/2020 | Hunter et al. |
| 10,610,223 | B2 | 4/2020 | Wellman et al. |
| 10,610,224 | B2 | 4/2020 | Shelton, IV et al. |
| 10,610,313 | B2 | 4/2020 | Bailey et al. |
| 10,617,412 | B2 | 4/2020 | Shelton, IV et al. |
| 10,624,635 | B2 | 4/2020 | Harris et al. |
| 10,631,858 | B2 | 4/2020 | Burbank |
| 10,631,859 | B2 | 4/2020 | Shelton, IV et al. |
| 10,639,034 | B2 | 5/2020 | Harris et al. |
| 10,639,035 | B2 | 5/2020 | Shelton, IV et al. |
| 10,639,037 | B2 | 5/2020 | Shelton, IV et al. |
| 10,653,413 | B2 | 5/2020 | Worthington et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |

(56) References Cited

U.S. PATENT DOCUMENTS 10,675,028 B2 6/2020 Shelton, IV et al.
10,682,136 B2 6/2020 Harris et al.
10,682,138 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,695,055 B2 6/2020 Shelton, IV et al.
10,695,057 B2 6/2020 Shelton, IV et al.
10,695,059 B2 6/2020 Kostrzewski
10,702,270 B2 7/2020 Shelton, IV et al.
10,709,446 B2 7/2020 Harris et al.
10,736,629 B2 8/2020 Shelton, IV et al.
10,758,229 B2 9/2020 Shelton, IV et al.
10,758,230 B2 9/2020 Shelton, IV et al.
10,758,232 B2 9/2020 Shelton, IV et al.
10,765,427 B2 9/2020 Shelton, IV et al.
10,772,629 B2 9/2020 Shelton, IV et al.
10,772,630 B2 9/2020 Wixey
10,779,823 B2 9/2020 Shelton, IV et al.
10,779,824 B2 9/2020 Shelton, IV et al.
10,779,826 B2 9/2020 Shelton, IV et al.
10,786,253 B2 9/2020 Shelton, IV et al.
10,806,530 B2 10/2020 Liao et al.
10,813,638 B2 10/2020 Shelton, IV et al.
10,835,245 B2 11/2020 Swayze et al.
10,835,246 B2 11/2020 Shelton, IV et al.
10,835,247 B2 11/2020 Shelton, IV et al.
10,856,867 B2 12/2020 Shelton, IV et al.
10,856,868 B2 12/2020 Shelton, IV et al.
10,856,869 B2 12/2020 Shelton, IV et al.
10,863,988 B2 12/2020 Patel et al.
10,881,401 B2 1/2021 Baber et al.
10,888,322 B2 1/2021 Morgan et al.
10,893,863 B2 1/2021 Shelton, IV et al.
10,893,864 B2 1/2021 Harris et al.
10,898,186 B2 1/2021 Bakos et al.
10,905,420 B2 2/2021 Jasemian et al.
10,918,385 B2 2/2021 Overmyer et al.
10,945,727 B2 3/2021 Shelton, IV et al.
10,959,726 B2 3/2021 Williams et al.
10,959,727 B2 3/2021 Hunter et al.
10,973,516 B2 4/2021 Shelton, IV et al.
10,973,517 B2 4/2021 Wixey
10,973,519 B2 4/2021 Wixey et al.
10,980,536 B2 4/2021 Weaner et al.
10,993,715 B2 5/2021 Shelton, IV et al.
10,993,716 B2 5/2021 Shelton, IV et al.
11,000,278 B2 5/2021 Shelton, IV et al.
11,000,279 B2 5/2021 Shelton, IV et al.
11,020,114 B2 6/2021 Shelton, IV et al.
11,020,138 B2 6/2021 Ragosta
11,020,193 B2 6/2021 Wixey et al.
11,026,755 B2 6/2021 Weir et al.
11,039,835 B2 6/2021 Wixey et al.
11,045,191 B2 6/2021 Shelton, IV et al.
11,058,424 B2 7/2021 Shelton, IV et al.
11,064,997 B2 7/2021 Shelton, IV et al.
11,064,999 B2 7/2021 Nelson et al.
11,076,926 B2 8/2021 Ragosta et al.
11,083,455 B2 8/2021 Shelton, IV et al.
11,090,048 B2 8/2021 Fanelli et al.
11,090,049 B2 8/2021 Bakos et al.
11,096,689 B2 8/2021 Overmyer et al.
11,129,611 B2 9/2021 Shelton, IV et al.
11,134,942 B2 10/2021 Harris et al.
11,134,944 B2 10/2021 Wise et al.
11,141,154 B2 10/2021 Shelton, IV et al.
11,147,552 B2 10/2021 Burbank et al.
11,160,551 B2 11/2021 Shelton, IV et al.
11,160,625 B2 11/2021 Wixey et al.
11,166,773 B2 11/2021 Ragosta et al.
11,179,155 B2 11/2021 Shelton, IV et al.
11,191,539 B2 12/2021 Overmyer et al.
11,191,540 B2 12/2021 Aronhalt et al.
11,191,543 B2 12/2021 Overmyer et al.
11,197,668 B2 12/2021 Shelton, IV et al.
11,207,064 B2 12/2021 Shelton, IV et al.
11,213,293 B2 1/2022 Worthington et al.
11,224,426 B2 1/2022 Shelton, IV et al.
11,224,428 B2 1/2022 Scott et al.
11,229,437 B2 1/2022 Shelton, IV et al.
11,234,700 B2 2/2022 Ragosta et al.
11,246,592 B2 2/2022 Shelton, IV et al.
11,259,805 B2 3/2022 Shelton, IV et al.
11,259,806 B2 3/2022 Shelton, IV et al.
11,259,807 B2 3/2022 Shelton, IV et al.
11,259,884 B2 3/2022 Burbank
11,266,405 B2 3/2022 Shelton, IV et al.
11,272,931 B2 3/2022 Boudreaux et al.
11,284,890 B2 3/2022 Nalagatla et al.
11,291,444 B2 4/2022 Boudreaux et al.
11,291,445 B2 4/2022 Shelton, IV et al.
11,298,129 B2 4/2022 Bakos et al.
11,298,130 B2 4/2022 Bakos et al.
11,311,293 B2 4/2022 Roberts et al.
11,317,913 B2 5/2022 Shelton, IV et al.
11,317,915 B2 5/2022 Boudreaux et al.
11,317,917 B2 5/2022 Shelton, IV et al.
11,324,503 B2 5/2022 Shelton, IV et al.
11,331,100 B2 5/2022 Boudreaux et al.
11,331,101 B2 5/2022 Harris et al.
11,357,503 B2 6/2022 Bakos et al.
11,364,029 B2 6/2022 Burbank et al.
11,369,377 B2 6/2022 Boudreaux et al.
11,389,161 B2 7/2022 Shelton, IV et al.
11,419,606 B2 8/2022 Overmyer et al.
11,439,390 B2 9/2022 Patel et al.
11,452,524 B2 9/2022 Chavan et al.
11,464,511 B2 10/2022 Timm et al.
11,478,242 B2 10/2022 Shelton, IV et al.
11,484,310 B2 11/2022 Shelton, IV et al.
11,497,494 B2 11/2022 Freidel et al.
11,504,124 B2 11/2022 Patel et al.
11,517,309 B2 12/2022 Bakos et al.
11,517,315 B2 12/2022 Huitema et al.
11,529,140 B2 12/2022 Shelton, IV et al.
11,540,826 B2 1/2023 Nalagatla et al.
11,564,688 B2 1/2023 Swayze et al.
11,571,210 B2 2/2023 Shelton, IV et al.
11,633,239 B2 4/2023 Ragosta et al.
11,653,915 B2 5/2023 Shelton, IV et al.
11,678,880 B2 6/2023 Shelton, IV et al.
11,696,759 B2 7/2023 Shelton, IV et al.
11,717,287 B2 8/2023 Williams et al.
11,730,475 B2 8/2023 Hudson et al.
11,751,871 B2 9/2023 Roberts et al.
11,751,872 B2 9/2023 Zeiner et al.
11,771,454 B2 10/2023 Swensgard et al.
11,779,327 B2 10/2023 Baxter, III et al.
11,779,332 B2 10/2023 Shelton, IV et al.
11,857,188 B2 1/2024 Hites
11,864,762 B2 1/2024 Wixey
11,896,202 B2 2/2024 Beckman et al.
11,925,350 B2 3/2024 Bakos et al.
11,944,297 B2 4/2024 Shelton, IV et al.
11,957,336 B2 4/2024 Shelton, IV et al.
11,974,741 B2 5/2024 Moubarak et al.
11,986,182 B2 5/2024 Shelton, IV et al.
11,986,184 B2 5/2024 Patel et al.
11,992,209 B2 5/2024 Shelton, IV et al.
11,992,210 B2 5/2024 Shelton, IV et al.
11,998,198 B2 6/2024 Shelton, IV et al.
12,011,164 B2 6/2024 Shelton, IV et al.
12,016,554 B2 6/2024 Laurent et al.
12,029,508 B2 7/2024 Shelton, IV et al.
12,089,842 B2 9/2024 Shelton, IV et al.
12,089,844 B2 9/2024 Patel et al.
12,102,321 B2 10/2024 Shelton, IV et al.
12,171,428 B2 12/2024 Shelton, IV et al.
12,213,668 B2 2/2025 Shelton, IV et al.
12,245,764 B2 3/2025 Overmyer et al.
12,251,105 B2 3/2025 Parks et al.
12,274,442 B2 4/2025 Scott et al.
12,324,583 B2 6/2025 Scott et al.

(56) References Cited

U.S. PATENT DOCUMENTS

| | | | |
|---|---|---|---|
| 12,446,880 B2 | 10/2025 | Shelton, IV et al. | |
| 12,484,900 B2 | 12/2025 | Ryle et al. | |
| 12,521,116 B2 | 1/2026 | Shelton, IV et al. | |
| 2001/0029384 A1 | 10/2001 | Nicholas et al. | |
| 2002/0066764 A1 | 6/2002 | Perry et al. | |
| 2003/0083673 A1 | 5/2003 | Tierney et al. | |
| 2005/0023324 A1 | 2/2005 | Doll et al. | |
| 2005/0131390 A1 | 6/2005 | Heinrich et al. | |
| 2005/0222616 A1 | 10/2005 | Rethy et al. | |
| 2006/0081678 A1 | 4/2006 | Ehrenfels et al. | |
| 2006/0185682 A1 | 8/2006 | Marczyk | |
| 2007/0039995 A1 | 2/2007 | Schwemberger et al. | |
| 2007/0102475 A1* | 5/2007 | Ortiz | A61B 17/07207 227/19 |
| 2007/0175955 A1 | 8/2007 | Shelton et al. | |
| 2007/0175956 A1 | 8/2007 | Swayze et al. | |
| 2007/0225562 A1 | 9/2007 | Spivey et al. | |
| 2008/0308603 A1 | 12/2008 | Shelton et al. | |
| 2009/0062814 A1 | 3/2009 | Omori et al. | |
| 2009/0308909 A1 | 12/2009 | Nalagatla et al. | |
| 2010/0065604 A1 | 3/2010 | Weng | |
| 2011/0290853 A1 | 12/2011 | Shelton, IV et al. | |
| 2012/0199632 A1 | 8/2012 | Spivey et al. | |
| 2012/0298719 A1 | 11/2012 | Shelton, IV et al. | |
| 2013/0248577 A1 | 9/2013 | Leimbach et al. | |
| 2013/0274722 A1 | 10/2013 | Kostrzewski et al. | |
| 2013/0277410 A1 | 10/2013 | Fernandez et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffman | |
| 2014/0239047 A1 | 8/2014 | Hodgkinson et al. | |
| 2014/0243801 A1 | 8/2014 | Fanelli et al. | |
| 2014/0246475 A1 | 9/2014 | Hall et al. | |
| 2014/0249557 A1 | 9/2014 | Koch, Jr. et al. | |
| 2014/0263541 A1 | 9/2014 | Leimbach et al. | |
| 2014/0263550 A1* | 9/2014 | Aranyi | A61B 17/07207 227/175.3 |
| 2014/0263552 A1 | 9/2014 | Hall et al. | |
| 2014/0263569 A1 | 9/2014 | Williams et al. | |
| 2015/0173789 A1 | 6/2015 | Baxter, III et al. | |
| 2015/0235357 A1 | 8/2015 | Nagashima et al. | |
| 2015/0272557 A1 | 10/2015 | Overmyer et al. | |
| 2015/0272571 A1 | 10/2015 | Leimbach et al. | |
| 2015/0272576 A1 | 10/2015 | Cappola et al. | |
| 2015/0272580 A1 | 10/2015 | Leimbach et al. | |
| 2015/0272582 A1 | 10/2015 | Leimbach et al. | |
| 2016/0066913 A1 | 3/2016 | Swayze et al. | |
| 2016/0249910 A1 | 9/2016 | Shelton, IV et al. | |
| 2016/0345971 A1 | 12/2016 | Bucciaglia et al. | |
| 2017/0224332 A1 | 8/2017 | Hunter et al. | |
| 2017/0231628 A1 | 8/2017 | Shelton, IV et al. | |
| 2017/0281186 A1 | 10/2017 | Shelton, IV et al. | |
| 2017/0296170 A1 | 10/2017 | Shelton, IV et al. | |
| 2018/0008265 A1 | 1/2018 | Hatanaka et al. | |
| 2018/0168575 A1 | 6/2018 | Simms et al. | |
| 2018/0168576 A1 | 6/2018 | Hunter et al. | |
| 2018/0168577 A1 | 6/2018 | Aronhalt et al. | |
| 2018/0168579 A1 | 6/2018 | Aronhalt et al. | |
| 2018/0168598 A1 | 6/2018 | Shelton, IV et al. | |
| 2018/0168608 A1 | 6/2018 | Shelton, IV et al. | |
| 2018/0168609 A1 | 6/2018 | Fanelli et al. | |
| 2018/0168615 A1 | 6/2018 | Shelton, IV et al. | |
| 2018/0168618 A1 | 6/2018 | Scott et al. | |
| 2018/0168619 A1 | 6/2018 | Scott et al. | |
| 2018/0168621 A1* | 6/2018 | Shelton, IV | A61B 34/30 |
| 2018/0168623 A1 | 6/2018 | Simms et al. | |
| 2018/0168625 A1 | 6/2018 | Posada et al. | |
| 2018/0168633 A1 | 6/2018 | Shelton, IV et al. | |
| 2018/0168647 A1 | 6/2018 | Shelton, IV et al. | |
| 2018/0168648 A1 | 6/2018 | Shelton, IV et al. | |
| 2018/0168650 A1 | 6/2018 | Shelton, IV et al. | |
| 2018/0168651 A1 | 6/2018 | Shelton, IV et al. | |
| 2018/0368844 A1 | 12/2018 | Bakos et al. | |
| 2019/0000458 A1* | 1/2019 | Shelton, IV | A61B 17/07207 |
| 2019/0000459 A1 | 1/2019 | Shelton, IV et al. | |
| 2019/0000461 A1 | 1/2019 | Shelton, IV et al. | |
| 2019/0076143 A1 | 3/2019 | Smith | |
| 2019/0125343 A1* | 5/2019 | Wise | A61B 17/07207 |
| 2019/0137349 A1 | 5/2019 | Collins et al. | |
| 2019/0239967 A1 | 8/2019 | Ragosta et al. | |
| 2019/0298354 A1* | 10/2019 | Shelton, IV | A61B 17/34 |
| 2020/0138435 A1* | 5/2020 | Shelton, IV | A61B 17/105 |
| 2020/0222044 A1 | 7/2020 | Baxter, III et al. | |
| 2021/0186495 A1 | 6/2021 | Shelton, IV et al. | |
| 2021/0378669 A1 | 12/2021 | Shelton, IV et al. | |
| 2022/0031351 A1 | 2/2022 | Moubarak et al. | |
| 2022/0061841 A1 | 3/2022 | Wixey et al. | |
| 2022/0071632 A1 | 3/2022 | Patel et al. | |
| 2022/0304682 A1 | 9/2022 | Shelton, IV et al. | |
| 2023/0052307 A1 | 2/2023 | Shelton, IV et al. | |
| 2023/0121131 A1 | 4/2023 | Swayze et al. | |
| 2024/0065690 A1 | 2/2024 | Jasemian et al. | |
| 2024/0197317 A1 | 6/2024 | Moubarak et al. | |
| 2024/0350137 A1 | 10/2024 | Fanelli et al. | |
| 2025/0025158 A1 | 1/2025 | Ryle et al. | |
| 2025/0082328 A1 | 3/2025 | Shelton, IV et al. | |
| 2025/0195066 A1 | 6/2025 | Parks et al. | |
| 2025/0261939 A1 | 8/2025 | Swayze et al. | |
| 2025/0261943 A1 | 8/2025 | Shelton, IV et al. | |
| 2025/0312043 A1 | 10/2025 | Shelton, IV et al. | |
| 2025/0331851 A1 | 10/2025 | Mozloom, Jr. et al. | |
| 2025/0331853 A1 | 10/2025 | Mozloom, Jr. et al. | |
| 2025/0331854 A1 | 10/2025 | Mozloom, Jr. et al. | |
| 2025/0366855 A1 | 12/2025 | Mozloom, Jr. et al. | |
| 2026/0123931 A1 | 5/2026 | Wise et al. | |

OTHER PUBLICATIONS

International Search Report and Written Opinion dated Jan. 23, 2023, for International Application No. PCT/IB2022/057609, 15 pages.

U.S. Appl. No. 18/650,562, entitled "Surgical Stapler with Firing Lockout Feature Coupled to End Effector Knife," filed Apr. 30, 2024.

U.S. Appl. No. 18/650,653, entitled "Surgical Stapler with Firing Lockout Feature Coupled to End Effector Jaw," filed Apr. 30, 2024.

U.S. Appl. No. 18/650,836, entitled "Surgical Stapler with Firing Lockout Feature Coupled to End Effector Retainer," filed Apr. 30, 2024.

U.S. Appl. No. 19/029,025, entitled "Surgical Tool Comprising a Firing Beam with an Arm," filed Jan. 17, 2025.

U.S. Appl. No. 19/188,629, entitled "Firing Beam Head Having a Rotatable Lock," filed Apr. 24, 2025.

Non-Final Office Action dated Apr. 23, 2025, for U.S. Appl. No. 18/650,562, 17 pages.

Final Office Action dated Oct. 27, 2025, for U.S. Appl. No. 18/650,562, 24 pages.

Advisory Action dated Jan. 5, 2026, for U.S. Appl. No. 18/650,562, 3 pages.

Non-Final Office Action dated Mar. 18, 2026, for U.S. Appl. No. 18/650,562, 12 pages.

Non-Final Office Action dated Jan. 9, 2026, for U.S. Appl. No. 19/024,990, 12 pages.

Final Office Action dated Mar. 12, 2026, for U.S. Appl. No. 19/024,990, 12 pages.

Advisory Action dated Apr. 23, 2026, for U.S. Appl. No. 19/024,990, 3 pages.

Non-Final Office Action dated May 20, 2026, for U.S. Appl. No. 19/242,481, 9 pages.

International Search Report and Written Opinion dated Jul. 25, 2025, for International Application No. PCT/IB2025/054444, 15 pages.

* cited by examiner

SURGICAL STAPLER WITH ROTATABLE LOCKOUT COLLAR

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion that is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The surgical stapling features of the present disclosure seek to inhibit firing of a surgical stapler end effector when the end effector is loaded with a spent staple cartridge that has already been fired, and/or when a staple cartridge is entirely absent from the end effector. Specifically, such features of the present disclosure place the end effector in a lockout state that inhibits firing in either of such scenario. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

DETAILED DESCRIPTION

Figure 1:
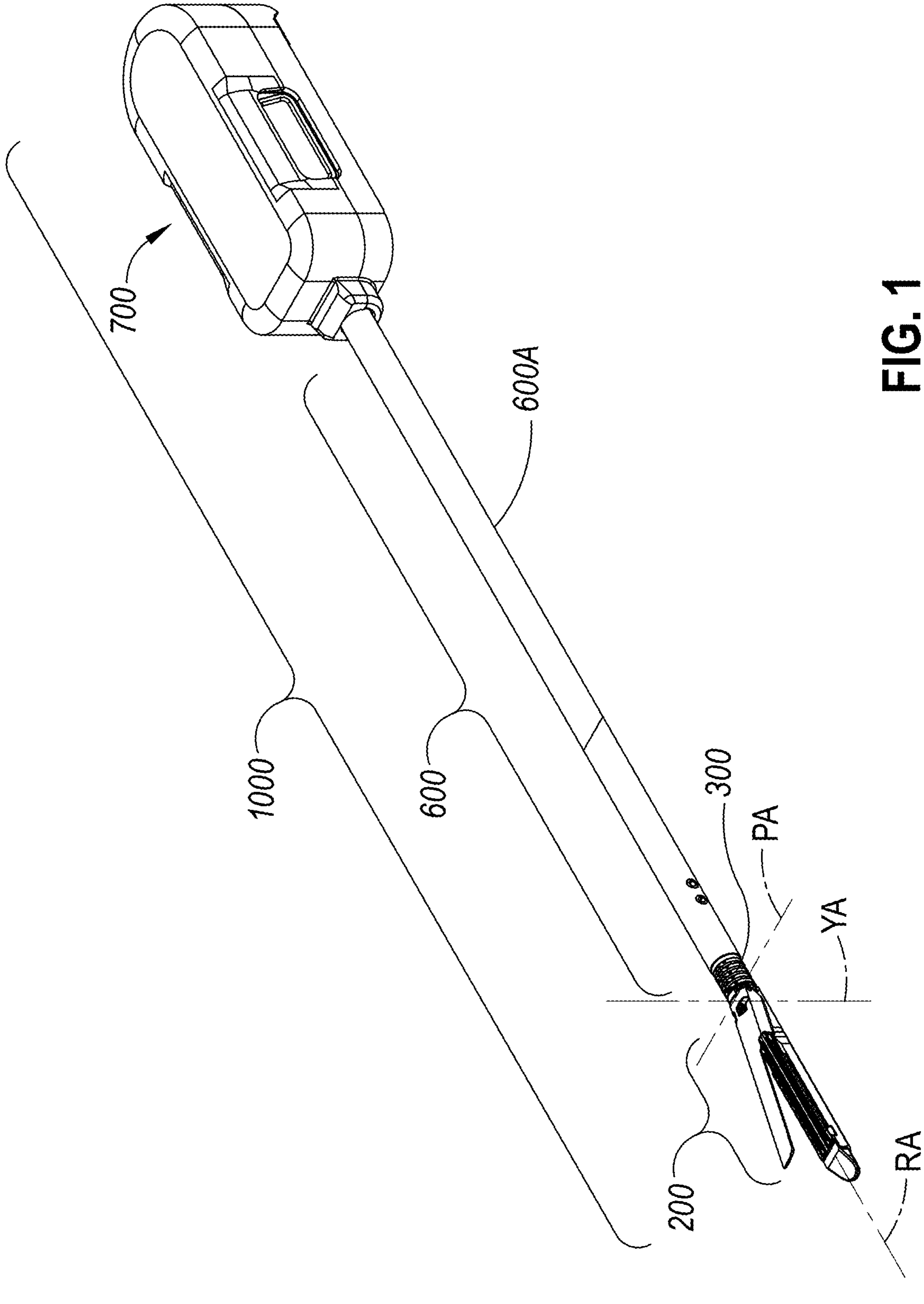
FIG. 1 is a perspective view of an illustrative surgical instrument having a housing, a shaft assembly, an articulation joint, and an end effector.

The following detailed description should be read with reference to the drawings, in which like elements in different drawings are identically numbered. The drawings, which are not necessarily to scale, depict selected versions and are not intended to limit the scope of the invention. The detailed description illustrates by way of example, not by way of limitation, the principles of the invention. This description will clearly enable one skilled in the art to make and use the invention, and describes several versions, adaptations, variations, alternatives and uses of the invention, including what is presently believed to be the best mode of carrying out the invention.

Numerous specific details are set forth to provide a thorough understanding of the overall structure, function, manufacture, and use of the versions as described in the specification and illustrated in the accompanying drawings. Well-known operations, components, and elements have not been described in detail so as not to obscure the versions described in the specification. The reader will understand that the versions described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a robotic platform manipulating the housing portion of the surgical instrument. The term "proximal" refers to the portion closest to the robotic platform and the term "distal" refers to the portion located away from the robotic platform. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures, and "substantially equal" values encompass nominally equal values.

Furthermore, the use of "couple", "coupled", or similar phrases should not be construed as being limited to a certain number of components or a particular order of components unless the context clearly dictates otherwise.

I. Overview of Illustrative Surgical Instrument

Figure 2:
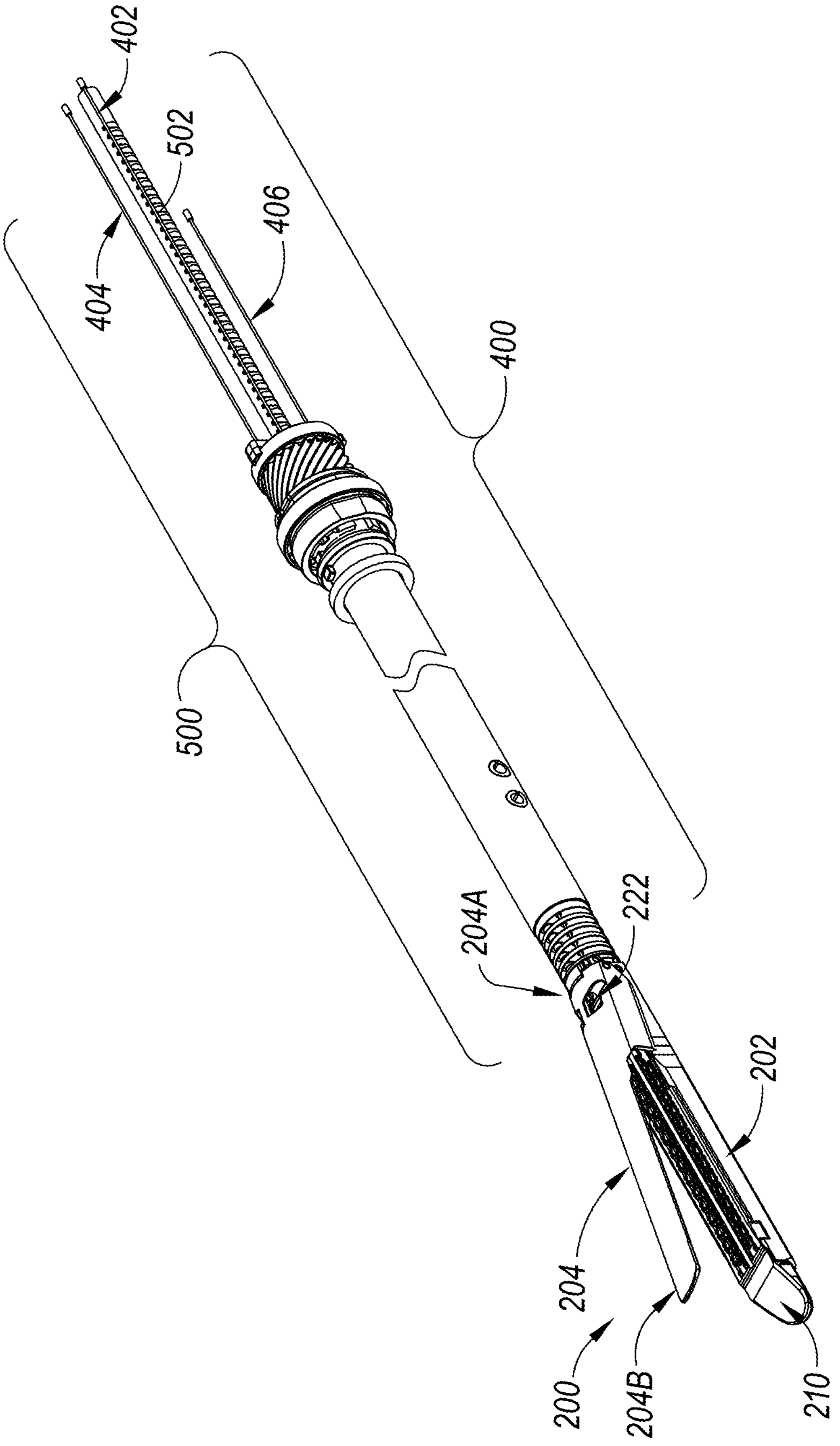
FIG. 2 is a partial perspective view of the surgical instrument of FIG. 1, with select components omitted from view to reveal portions of a cable articulation subsystem, a knife firing subsystem, and a roll subsystem of the surgical instrument.

FIGS. 1-2 show an illustrative surgical instrument 1000 that is configured to grasp, clamp, incise, and seal patient tissue with staples. The surgical instrument 1000 comprises an end effector 200, an articulation joint 300 (also referred to as a "continuum joint"), an articulation drive subsystem 400 configured to articulate the end effector 200 via the articulation joint 300, a knife firing subsystem 500 configured to actuate the end effector 200 between various positions (e.g., an open position, a grasping position, and a clamping position) and to incise and staple patient tissue, a roll subsystem 600 configured to rotate the end effector 200 about a roll axis RA, and a housing 700.

Figure 3:
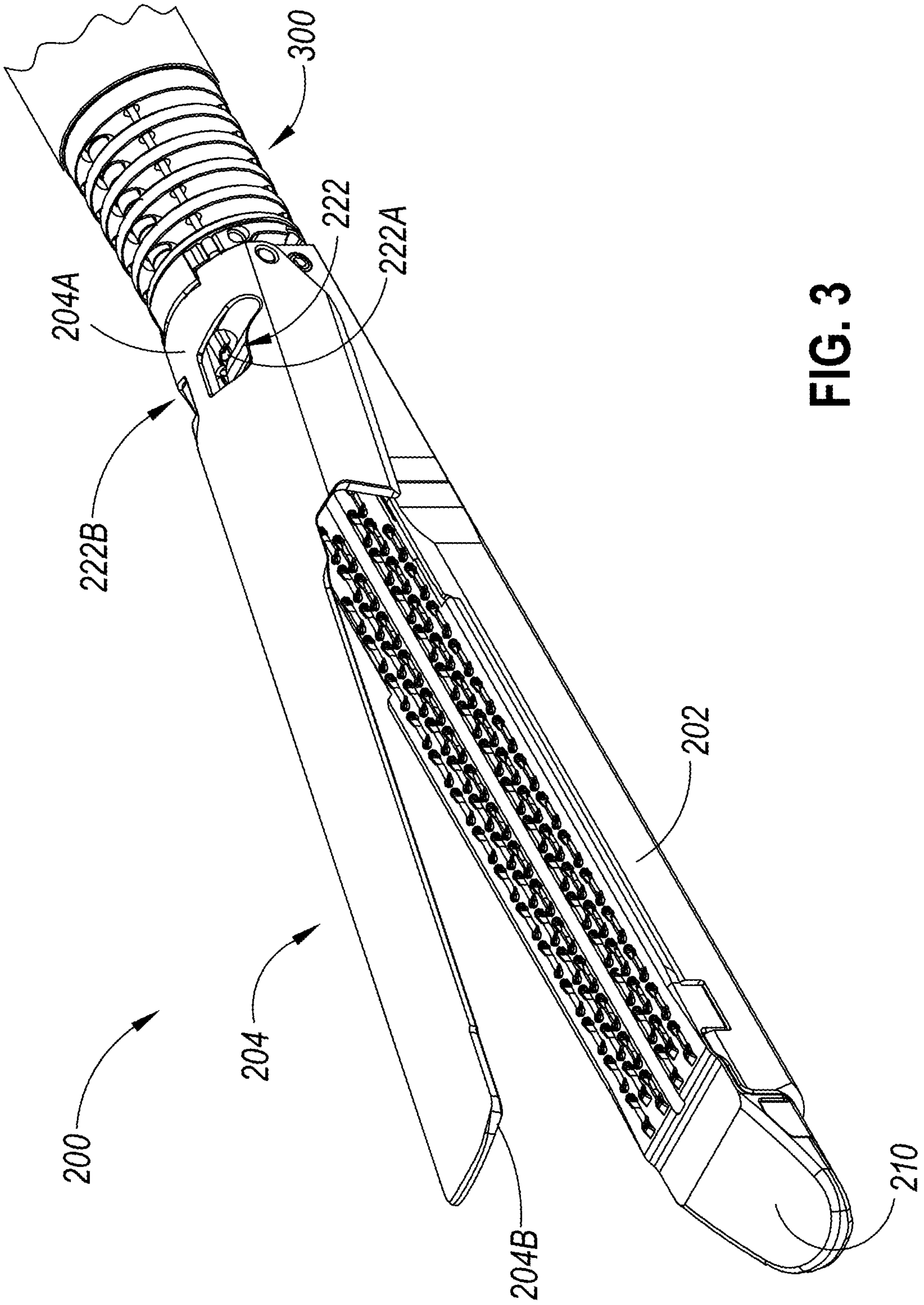
FIG. 3 is an enlarged perspective view of the end effector and the articulation joint of the surgical instrument of FIG. 1.
Figures 4, 5:
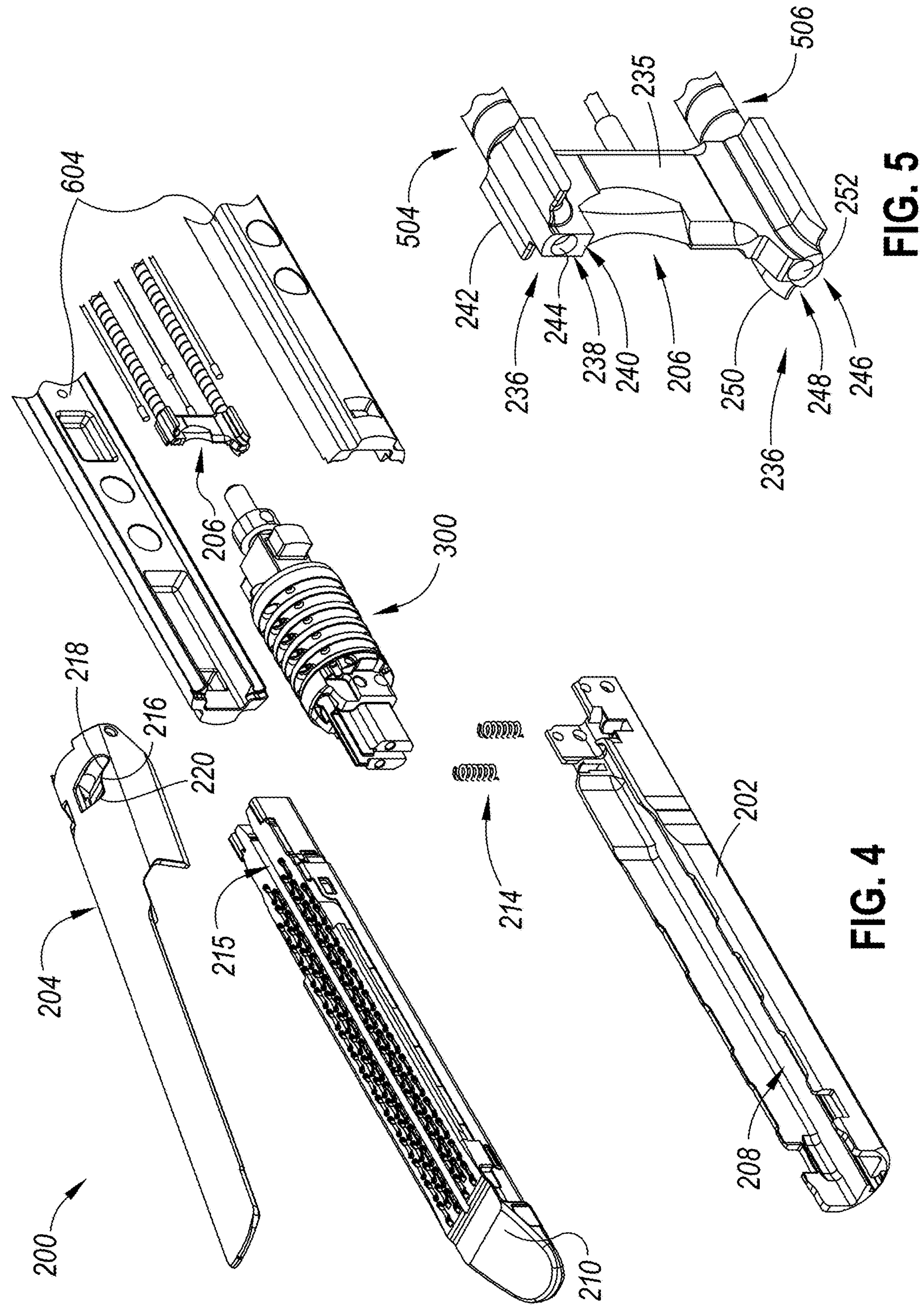
FIG. 4 is an exploded view of a distal end portion of the surgical instrument of FIG. 1.
FIG. 5 is an enlarged perspective view of a knife of the end effector of the surgical instrument of FIG. 1.
Figure 7:
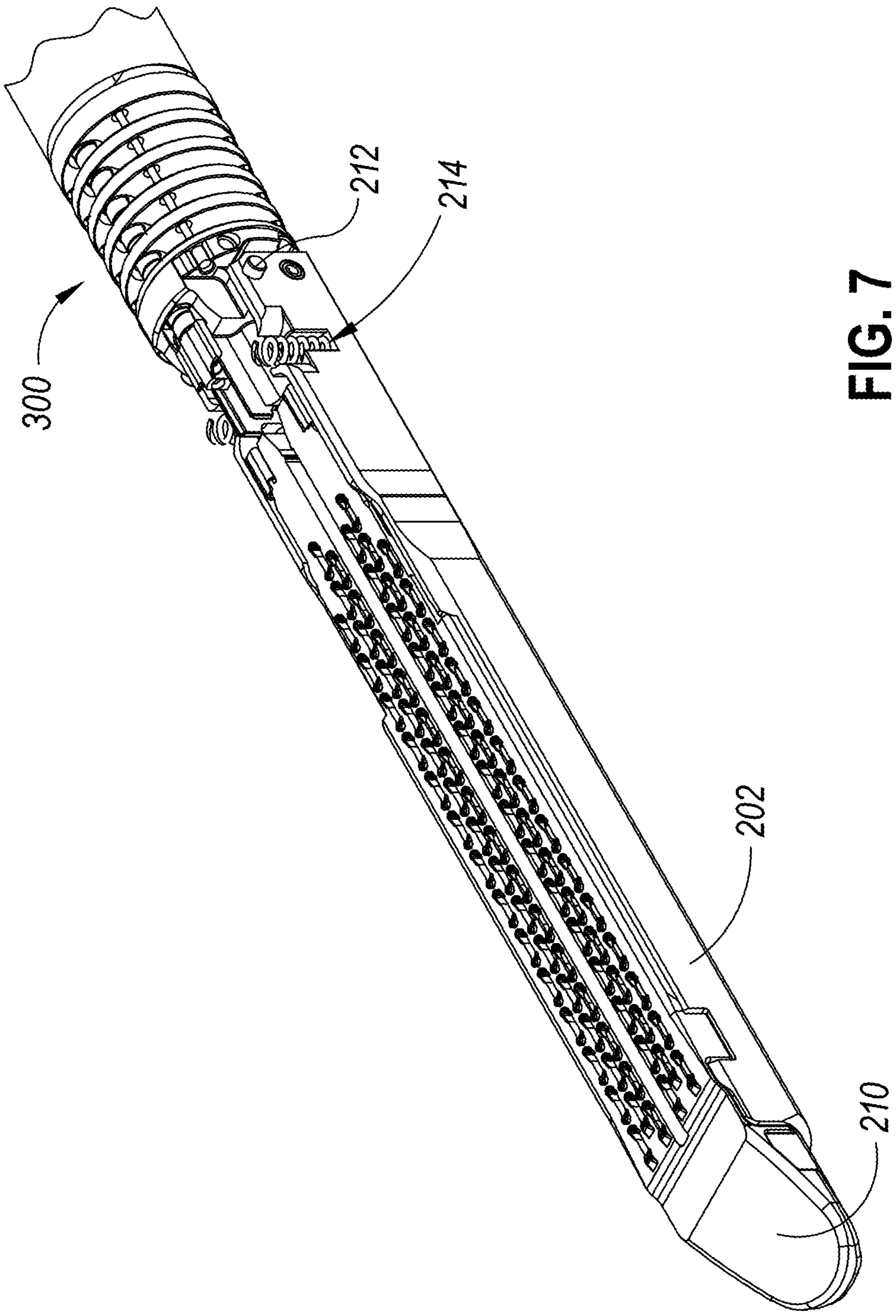
FIG. 7 is an enlarged perspective view of the end effector and the articulation joint of FIG. 3, with an anvil of the end effector omitted.

As shown best in FIGS. 3-4, the end effector 200 comprises a first jaw 202 (also known as a "cartridge jaw" or a "channel") and a second jaw 204 (also known as an "anvil jaw" or just "anvil") movable relative to the cartridge jaw 202 between an open position and a closed position. The cartridge jaw 202 and anvil jaw 204 may be elongated in form. The cartridge jaw 202 defines an elongated channel 208 for receiving a staple cartridge 210 (also known as a "reload"). The anvil jaw 204 has a proximal end 204A, a distal end 204B, and a ramp surface 216 defined at the proximal end 204A, which is described in greater detail below with respect to FIGS. 4 and 9A-9D. The cartridge jaw 202 and anvil jaw 204 are pivotally coupled via a pivot pin 212 that extends through the cartridge jaw 202 and the anvil jaw 204. As seen in FIG. 7, one or more biasing springs 214 extend between the cartridge jaw 202 and anvil jaw 204 to bias the anvil jaw 204 to the open position.

The ramp surface 216 may be visible via a kidney bean-shaped opening 222 (which may be formed as part of the manufacturing process to make the ramp surface 216) that has a first lateral end 222A and a second lateral end 222B. In other words, the kidney bean-shaped opening may be open at its lateral ends 222A, 222B (FIG. 3). As seen in FIG. 4, the ramp surface 216 forms a lower surface of the kidney bean-shaped opening 222. The ramp surface 216 can be arcuately shaped. For example, as shown particularly in FIGS. 4 and 9A-9D, it may be upwardly sloped at a first angle 218 and arcuately taper, in a distal direction, to a substantially horizontal second angle 220.

Figure 8A:
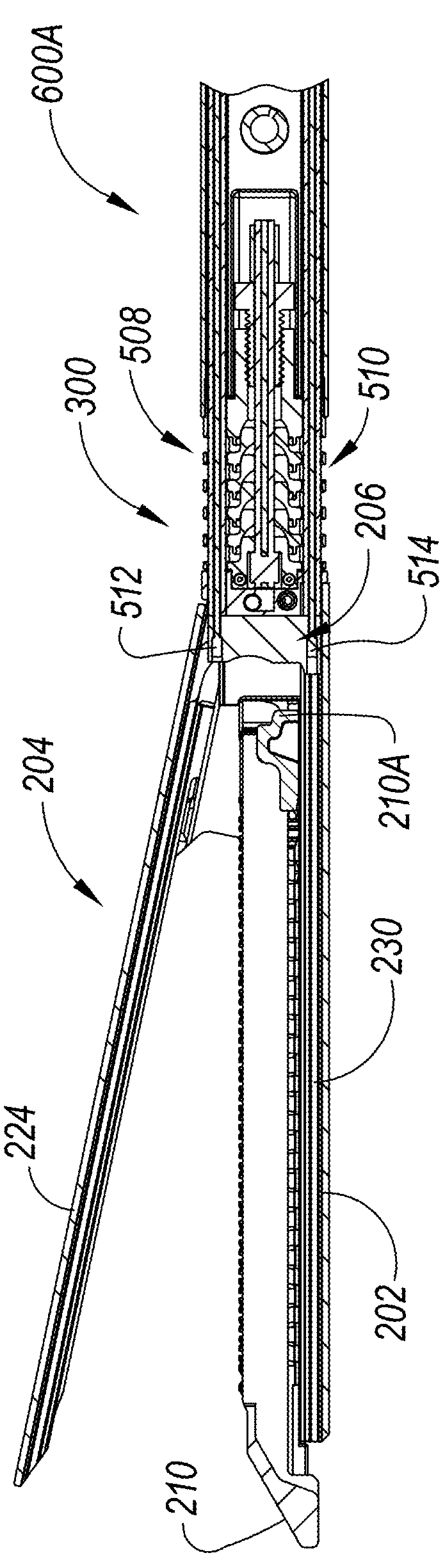
FIG. 8A is a side cross-sectional view of a distal end portion of the surgical instrument of FIG. 1, depicting the anvil in an open position.
Figure 8B:
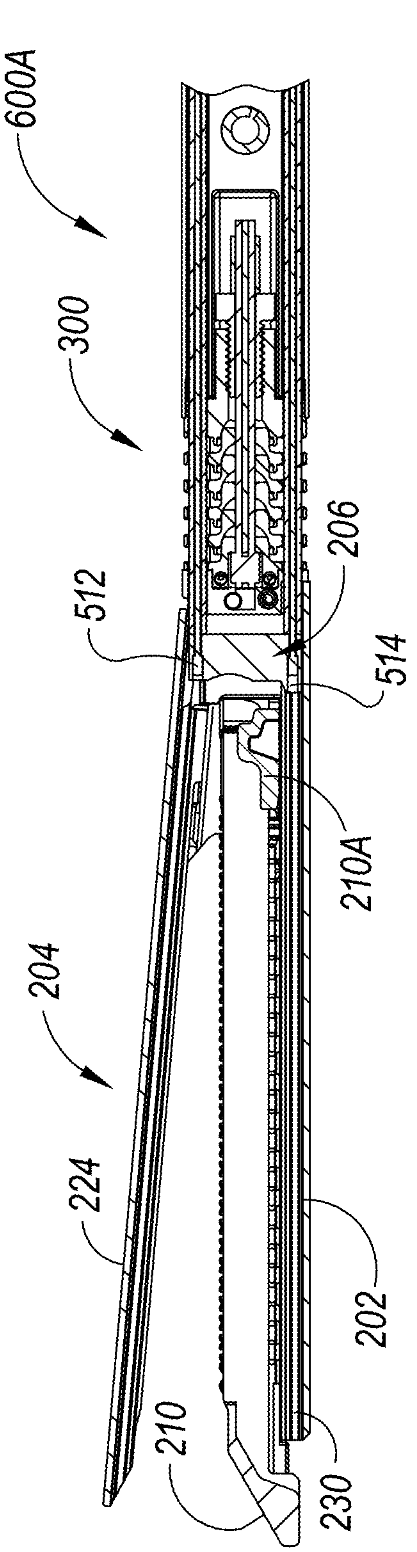
FIG. 8B is a side cross-sectional view of the distal end portion of the surgical instrument of FIG. 1, depicting the anvil in a grasping position with the knife partially advanced.

The anvil jaw 204 further defines a longitudinally extending upper knife channel 224 (see FIG. 8A, etc.). As shown particularly in FIG. 6, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

Figure 17:
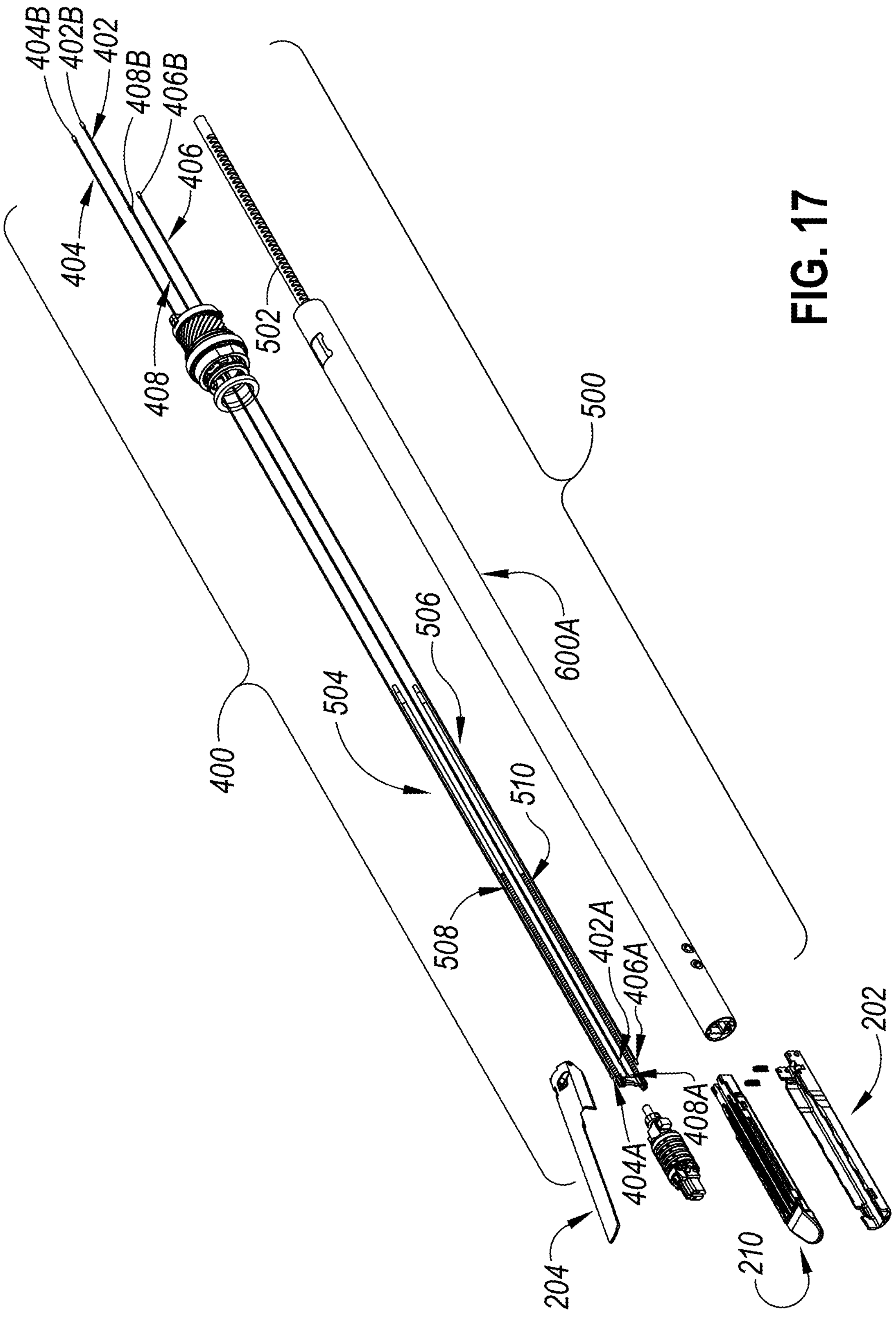
FIG. 17 is an exploded perspective view of a portion of the surgical instrument of FIG. 1, depicting portions of the cable articulation subsystem, the knife firing subsystem, and the roll subsystem.

As shown in FIGS. 2 and 17, the surgical instrument 1000 further comprises a knife firing subsystem 500 operable to close the anvil jaw 204 during a closure stroke. After the end effector 200 is closed, the knife firing subsystem 500 is operable to incise and staple, with staples from the staple cartridge 210, the patient tissue captured between the staple cartridge 210 (which is retained by the cartridge jaw 202) and anvil jaw 204 during a firing stroke.

Figure 6:
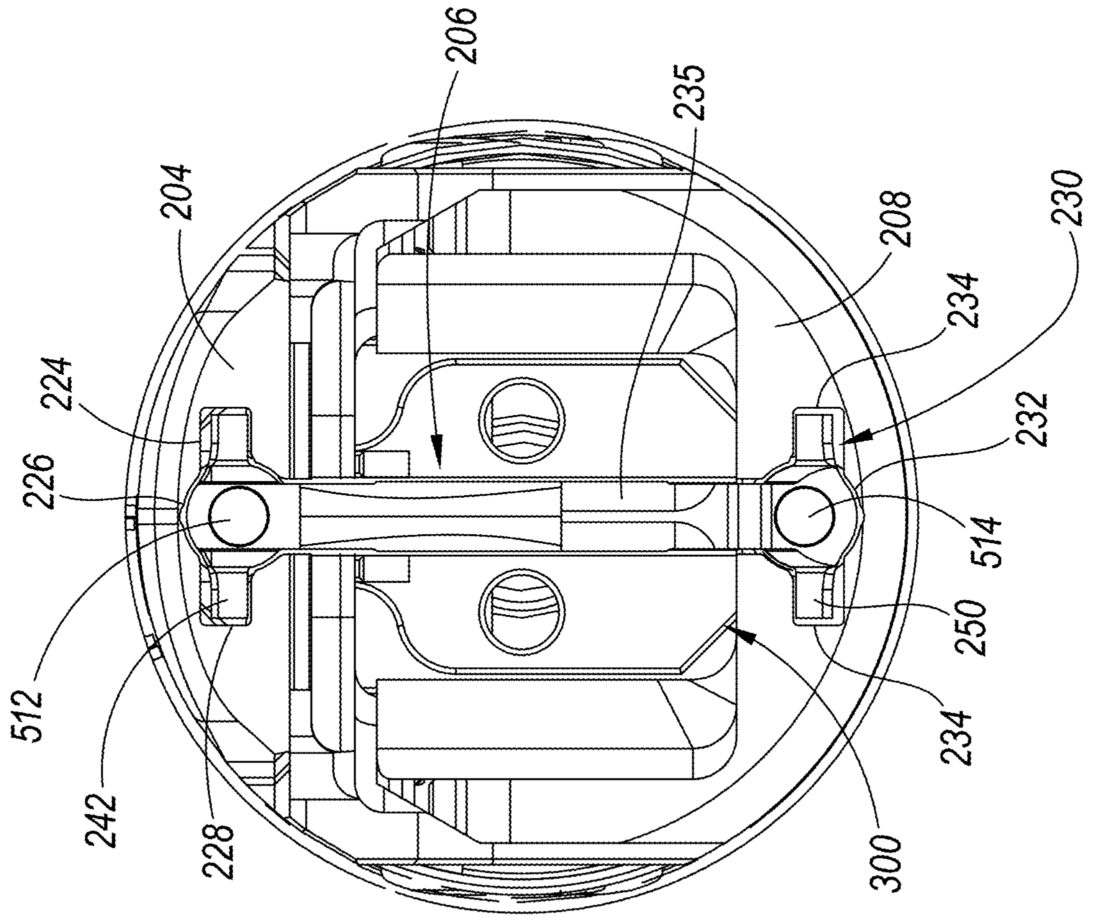
FIG. 6 is an end view of the end effector of FIG. 3.

As shown best in FIGS. 4-6, the knife firing subsystem 500, explained further below in greater detail, includes a knife 206 having a knife sled 236. The knife sled 236 functions as a firing driver by driving cartridge sled 210A distally through a firing stroke, as described below. In some instances, knife sled 236 may be referred to as an I-beam. The knife sled 236 includes an upper knife tab 238, a lower knife tab 246, and a vertical column 235 coupling and extending between upper knife tab 238 and lower knife tab 246. The upper knife tab 238 includes a centrally disposed cylindrical upper knife tab portion 240 and at least one upper knife tab lateral wing 242 that extends away from the upper knife tab portion 240. While the term 'cylindrical' is used, the tab portion need not resemble a perfect cylinder.

The upper knife tab 238 may include a pair of lateral wings 242 configured to slidably ride in the upper knife channel 224 to move the anvil jaw 204 between the open position, the grasping position, and the clamping position. Accordingly, the end effector 200 employs "knife-based closure" in which closure of the anvil jaw 204 relative to the cartridge jaw 202 is driven by distal advancement of the knife 206. Each lateral wing 242 may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some versions, the lower knife tab 246 includes a pair of lateral wings 250. The lower knife tab portion 248 defines a lower knife tab opening 252 that is configured to receive a barrel crimp coupled to a center cable 514, as described in greater detail below.

Figure 8C:
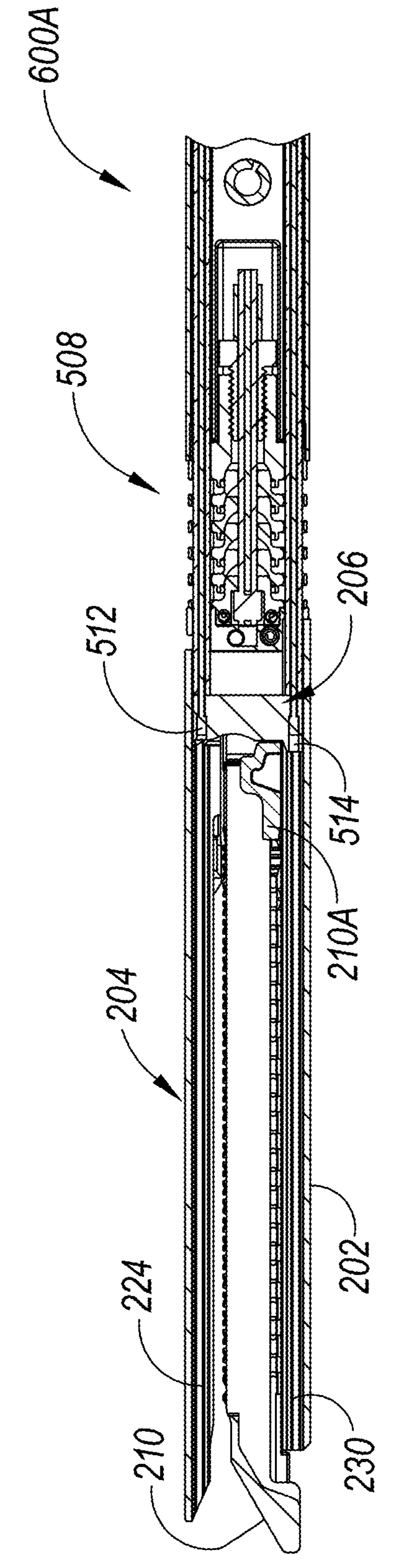
FIG. 8C is a side cross-sectional view of the distal end portion of the surgical instrument of FIG. 1, depicting the anvil in a clamping position with the knife partially advanced.
Figure 8D:
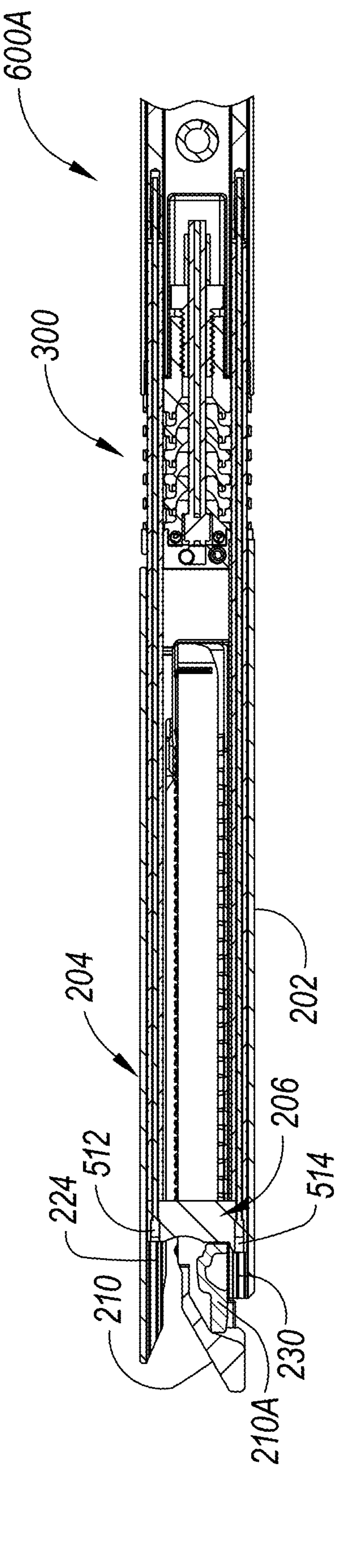
FIG. 8D is a side cross-sectional view of the distal end portion of the surgical instrument of FIG. 1, depicting the anvil in the clamping position with the knife fully advanced.

The staple cartridge 210 may be generally constructed and operable in accordance with the teachings of U.S. patent application Ser. No. 18/588,684, entitled "Methods of Surgical Stapling," filed on Feb. 27, 2024, issued as U.S. Pat. No. 12,471,913 on Nov. 18, 2025, the disclosure of which is incorporated by reference herein in its entirety. In use, the end effector 200 is positioned relative to patient tissue such that the staple cartridge 210 is disposed on a first side of the tissue and the anvil jaw 204 is positioned on an opposed second side of the tissue. The anvil jaw 204 is then approximated toward the staple cartridge 210 to compress and clamp the tissue against the deck of the staple cartridge 210. Thereafter, the surgical instrument 1000 is fired so that the knife 206 advances distally through the staple cartridge 210 to both cut the clamped tissue and simultaneously actuate staple drivers housed within the staple cartridge 210 to drive an array of staples into the clamped tissue on either side of the cut line. Staple cartridge 210 defines an elongate knife channel 215 dimensioned to receive a portion of vertical column 235 in order to accommodate advancement of knife 206 through staple cartridge 210. A portion of cartridge sled 210A is slidably housed within elongate knife channel 215 such that vertical column 235 drives cartridge sled 210A distally as knife 206 advances distally in accordance with the description herein (see FIGS. 8C-8D). In some instances, cartridge sled 210A remains in the distal position (see FIG. 8D) relative to the rest of staple cartridge 210, even after knife 206 is retracted proximally after firing staple cartridge 210 in accordance with the description herein.

As mentioned above, cartridge jaw 202 defines an elongated channel 208 for receiving staple cartridge 210. Additionally, cartridge jaw 202 also defines a lower knife channel 230 (see FIGS. 4, 6, and 8A-9D) dimensioned to slidably receive lower knife tab 246. Referring to FIG. 6, the lower knife channel 230 includes a centrally disposed cylindrical lower knife channel portion 232 and at least one lateral lower knife channel wing 234 that extends away from the lower knife channel portion 232. Cylindrical lower knife channel portion 232 is in communication with elongated channel 208 such that when staple cartridge 210 is suitably coupled to cartridge jaw 202, elongate knife channel 215 of staple cartridge 210 and centrally disposed cylindrical lower knife channel portion 232 are aligned to accommodate actuation of knife sled 236 within both channels 215, 230. Lateral lower knife channel wings 234 are dimensioned to slidably house a respective lower knife tab lateral wing 250. Lower knife tab lateral wings 250 are configured to slidably contact lateral lower knife channel wings 234 as knife 206 is advanced in accordance with the description herein. Contact between lower knife tab lateral wings 250 and lateral lower knife channel wings 234 cooperatively assists lateral wings 242 and upper knife channel 224 to close anvil jaw 204 relative to channel 208 in accordance with the description herein. While the term 'cylindrical' is used, the channel portion 232 need not resemble a perfect cylinder. Other arrangements of staple cavities and staples may be possible. For example, in some versions, a lower knife channel 230 can be defined in the cartridge jaw 202.

Further to the above, the knife sled 236 is moved distally and proximally by a firing rod 502. The firing rod 502 is configured to apply an indirect force to the knife sled 236, via push coils 508, 510 that directly engage the knife sled 236 (discussed in greater detail below), and push the knife sled 236 toward the distal end of the end effector 200 through a firing stroke. As the firing rod 502 is advanced distally, knife sled 236 rides in the lower knife channel 230 and the upper knife channel 224. At the onset of travel, the upper knife tab 238 rides along the anvil ramp surface 216. Specifically, as particularly seen in the sequence of FIGS. 8A-8D and 9A-9D, movement of the knife sled 236 distally causes the upper knife tab ramped surface 242A to slide along the anvil ramp surface 216. This movement first urges the anvil jaw 204 closed to a position (e.g., FIGS. 8B and 9B) where a compressive force is applied to the tissue sufficient to grasp it (referred to as the grasping position). Continued movement of the knife sled 236 up the ramp surface 216 (e.g., see FIGS. 8C and 9C) results in a compressive force being applied to the tissue (referred to as the clamping position). As the anvil ramp surface 216 transitions to its substantially horizontally angled surface 220 (e.g., see FIGS. 8D and 9D), the upper knife tab 238 can slide within the upper knife channel 224 to drive the stapling and transection of the tissue.

Figure 18:
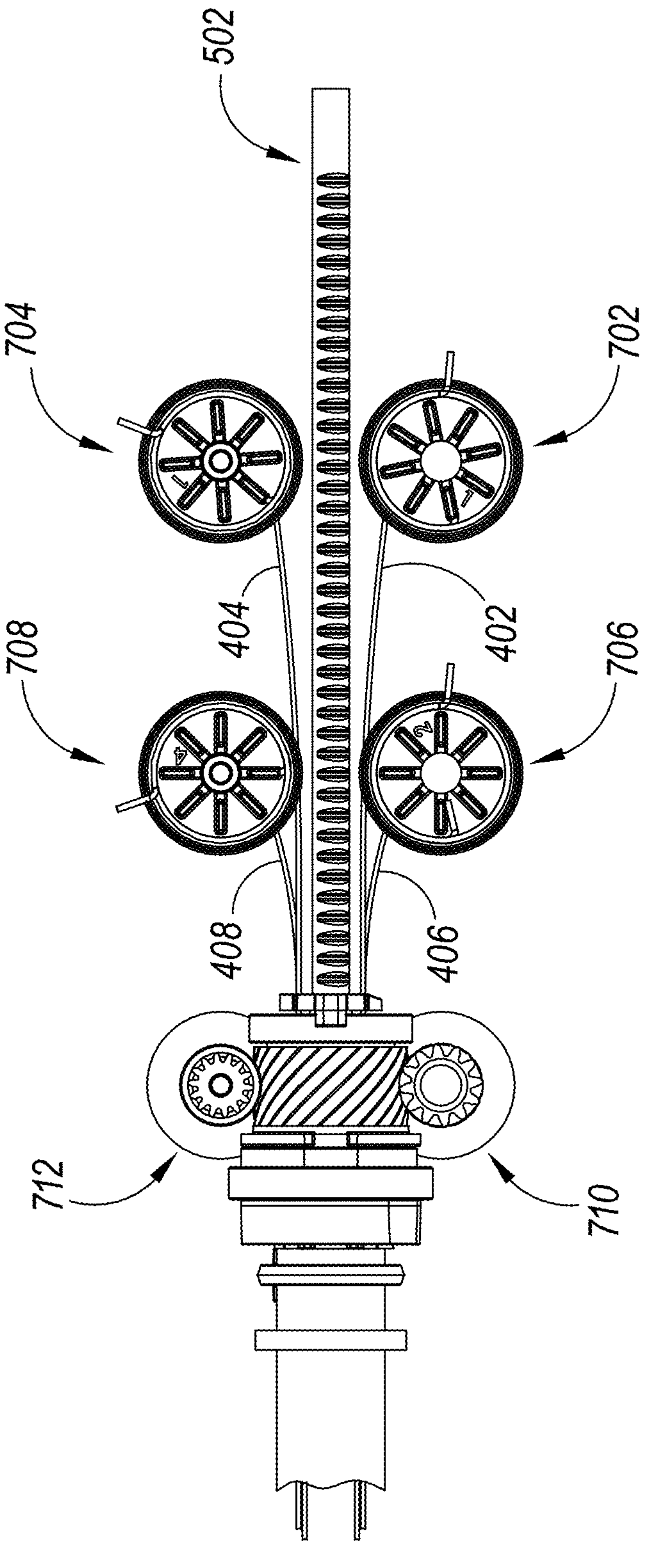
FIG. 18 is a top view of a proximal end of the surgical instrument of FIG. 1, depicting portions of the cable articulation subsystem, the knife firing subsystem, and the roll subsystem.
Figure 19:
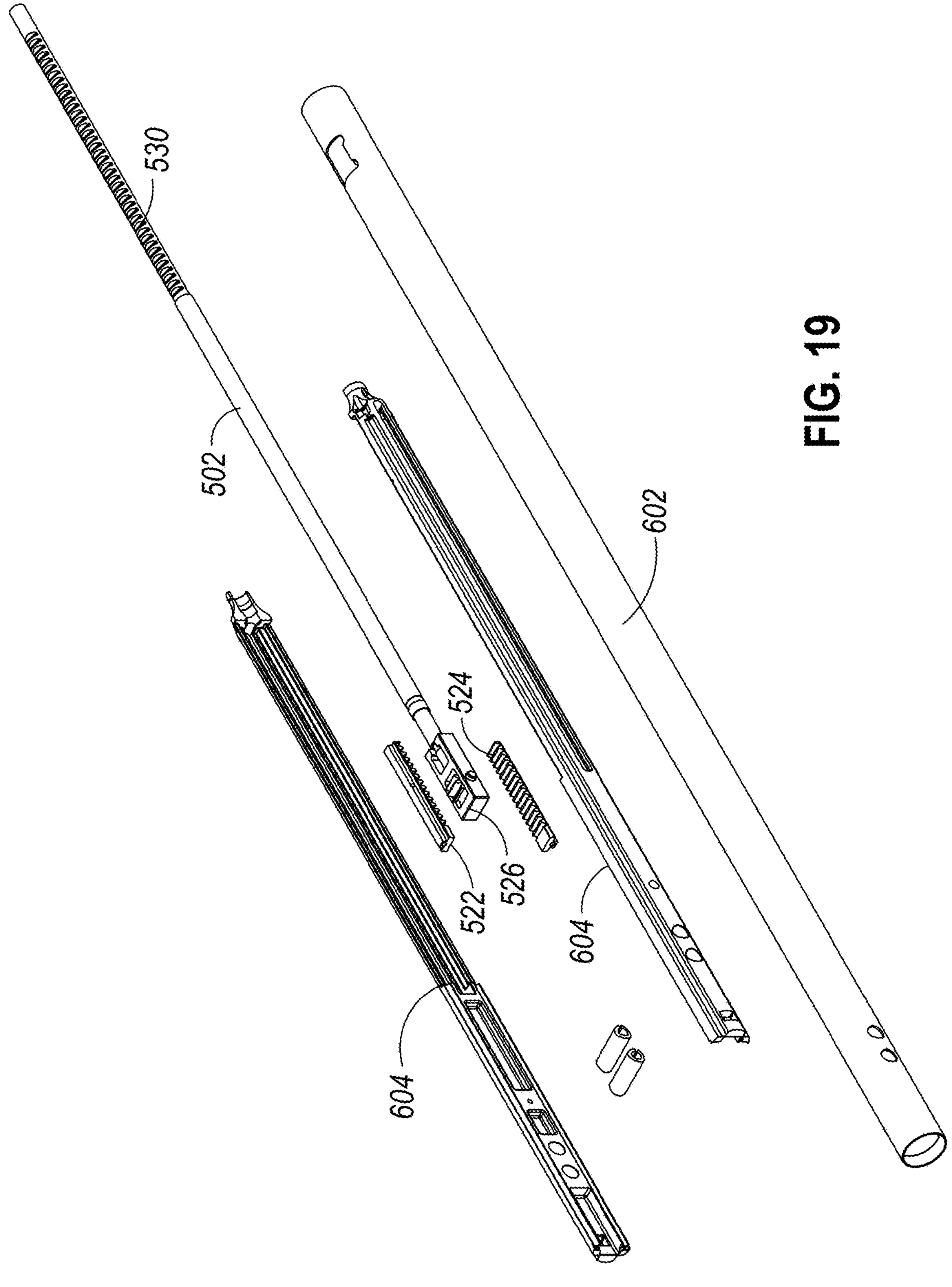
FIG. 19 is a perspective view of a shaft assembly, a differential, and a firing rod of the surgical instrument of FIG. 1.
Figure 20:
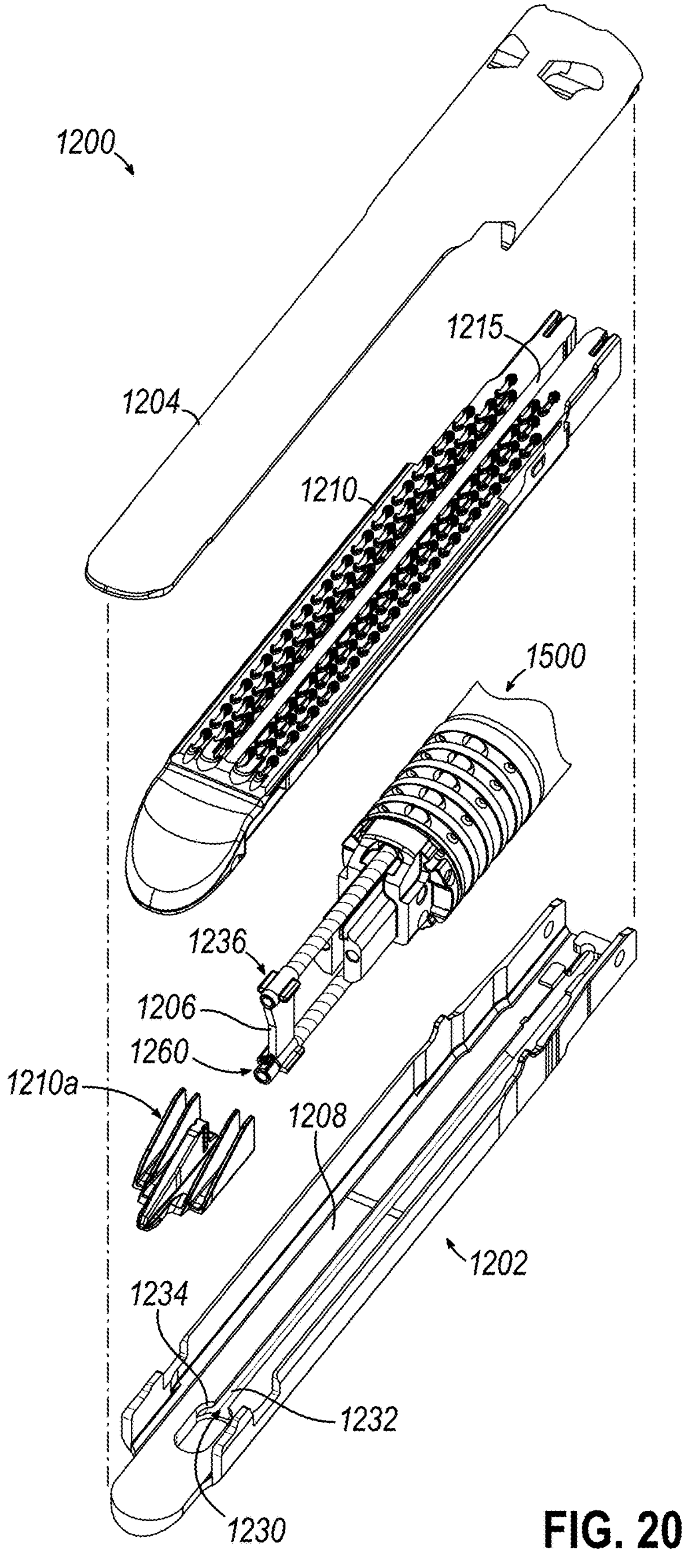
FIG. 20 is an exploded perspective view of an alternative end effector having a knife and a knife lockout assembly.
Figure 21:
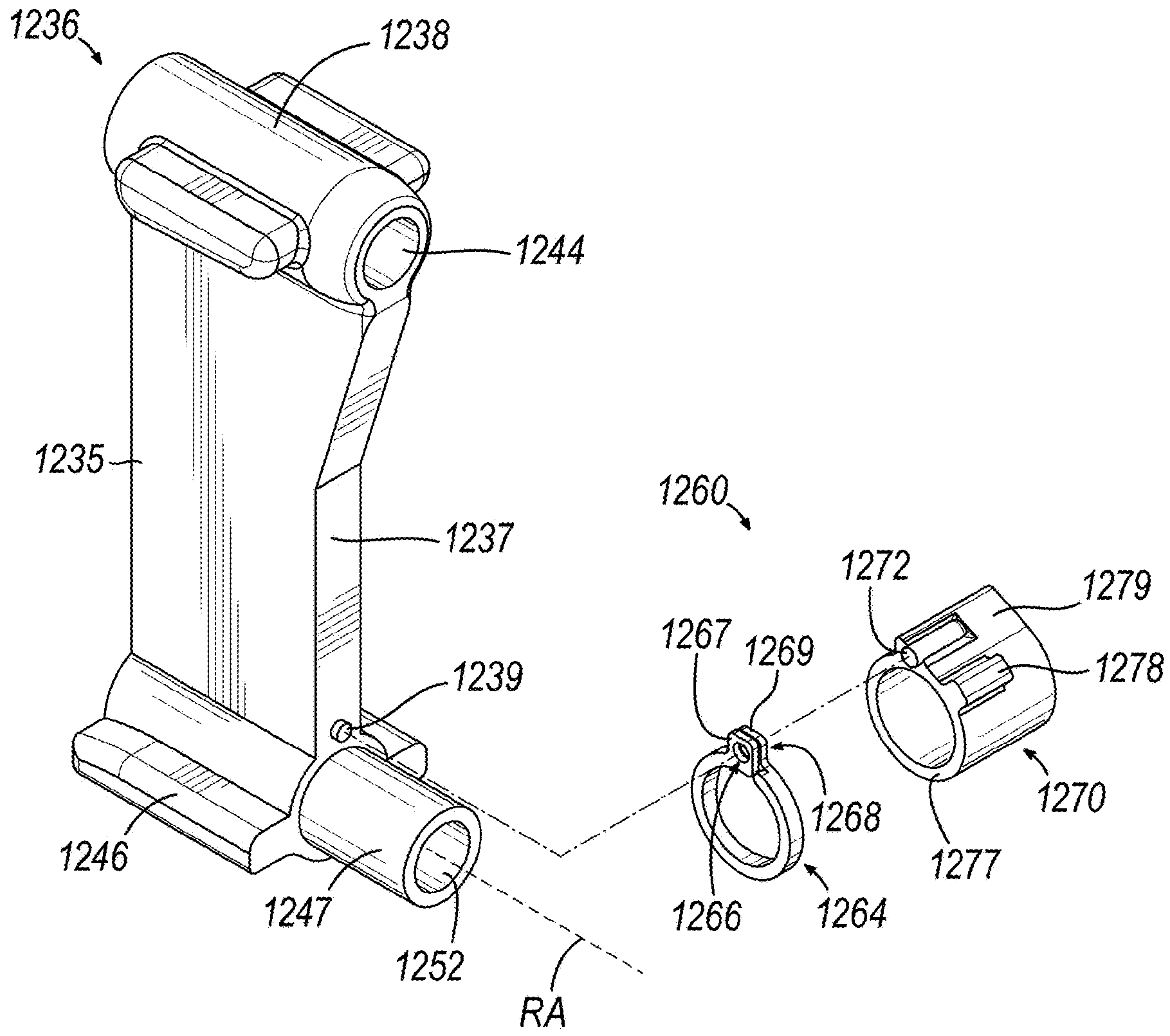
FIG. 21 is an exploded perspective view of the knife and the knife lockout assembly of FIG. 20.

As shown in FIG. 1, the surgical instrument 1000 further comprises a body exemplified as a housing 700 configured to engage a robotic platform (not shown). In other versions, the body may be configured as a handle configured to be gripped and manipulated by a clinician. As best shown in FIGS. 1 and 19, a shaft assembly 600A extends distally from the housing 700 and includes a rotatable outer shaft 602 and an inner shaft 604 arranged in two clamshell halves, with the outer shaft 602 being rotatably mounted to the housing 700 about a rotation joint (not shown), which may include one or more bearings. The inner shaft 604 is rotationally fixed to the outer shaft 602 and is configured such that articulation cables 402, 404, 406, 408 can be partially wound therearound without becoming tangled. As shown in FIG. 18, the housing 700 may house (1) a firing puck assembly 712 as part of the knife firing subsystem 500 operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602.

Referring to FIGS. 10-13, the articulation joint 300 comprises an array of joint discs 302 arranged longitudinally, and a center beam assembly 306 that cooperates with the joint discs 302 to provide articulation of the end effector 200 with at least two degrees of freedom (e.g., yaw and pitch), as described further below. Each joint disc 302 includes a central opening 304 that is configured to align coaxially with the central opening 304 of the other joint discs when the articulation joint 300 is in a straight, non-articulated state. The center beam assembly 306 extends longitudinally through the central openings 304 of joint discs 302 and applies a compressive axial force to the array of joints discs 302 to couple the joint discs 302 with one another. The joint discs 302 are nestably stacked with one another along the center beam assembly 306 such that longitudinally adjacent joint discs 302 movably interface with one another.

Figure 9B:
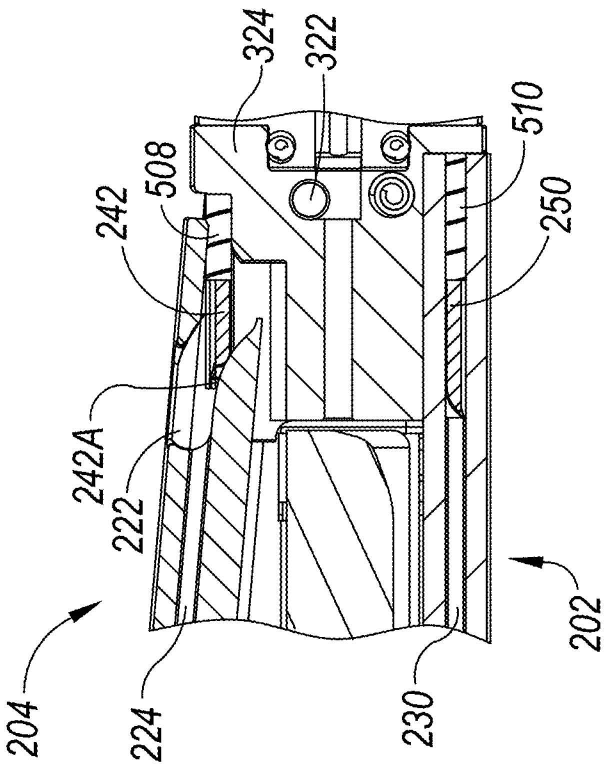
FIG. 9B is an enlarged side cross-sectional view of the proximal end portion of the end effector of the surgical instrument of FIG. 1, depicting the anvil in a grasping position with the knife partially advanced.
Figure 9A:
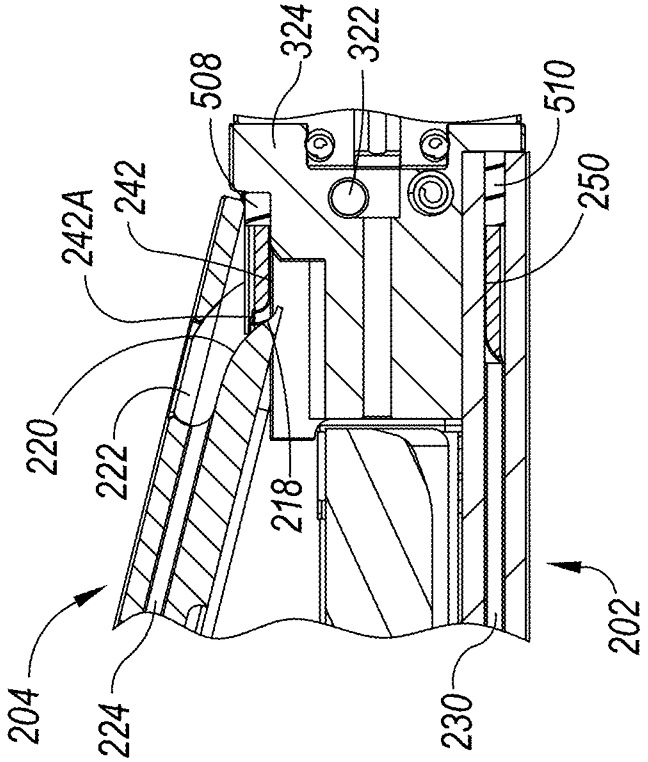
FIG. 9A is an enlarged side cross-sectional view of a proximal end portion of the end effector of the surgical instrument of FIG. 1, depicting the anvil in the open position.
Figure 9D:
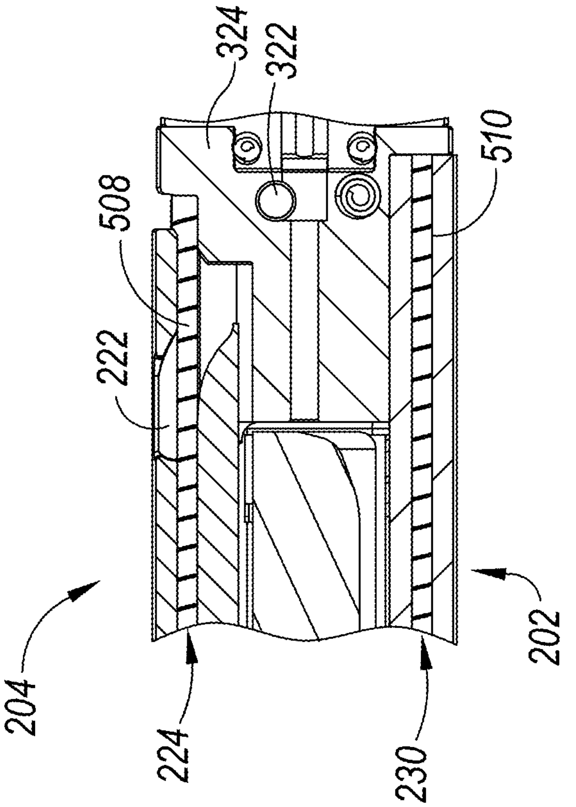
FIG. 9D is an enlarged side cross-sectional view of the proximal end portion of the end effector of the surgical instrument of FIG. 1, depicting the anvil in the clamping position with the knife fully advanced.
Figure 9C:
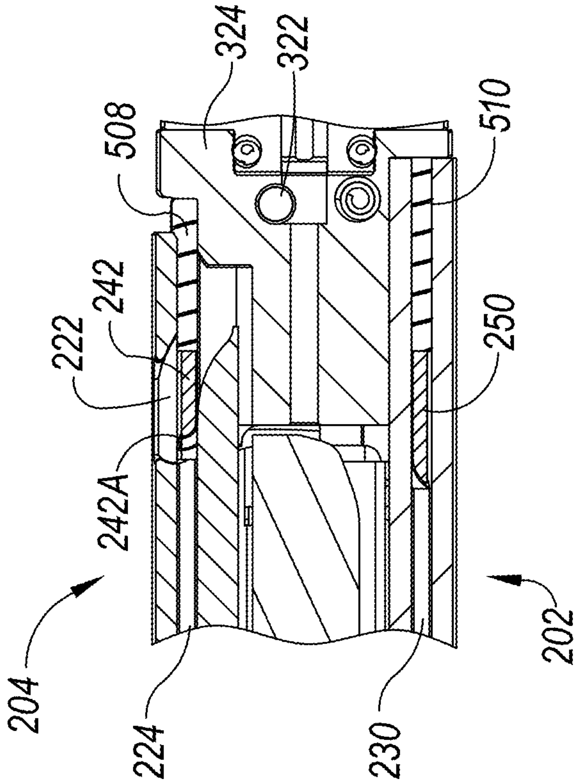
FIG. 9C is an enlarged side cross-sectional view of the proximal end portion of the end effector of the surgical instrument of FIG. 1, depicting the anvil in a clamping position with the knife partially advanced.
Figure 10:
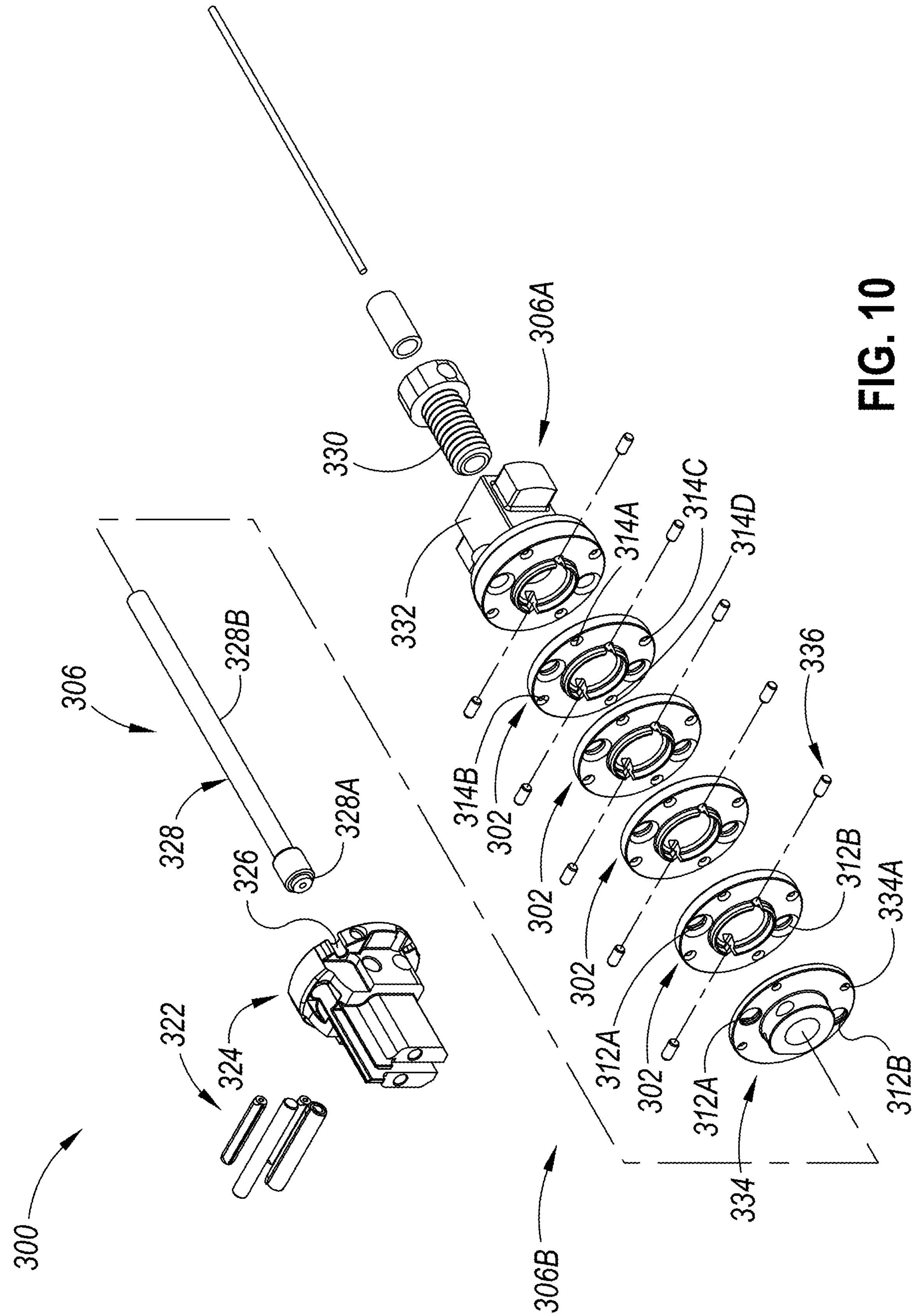
FIG. 10 is an exploded perspective view of the articulation joint of the surgical instrument of FIG. 1.
Figure 11:
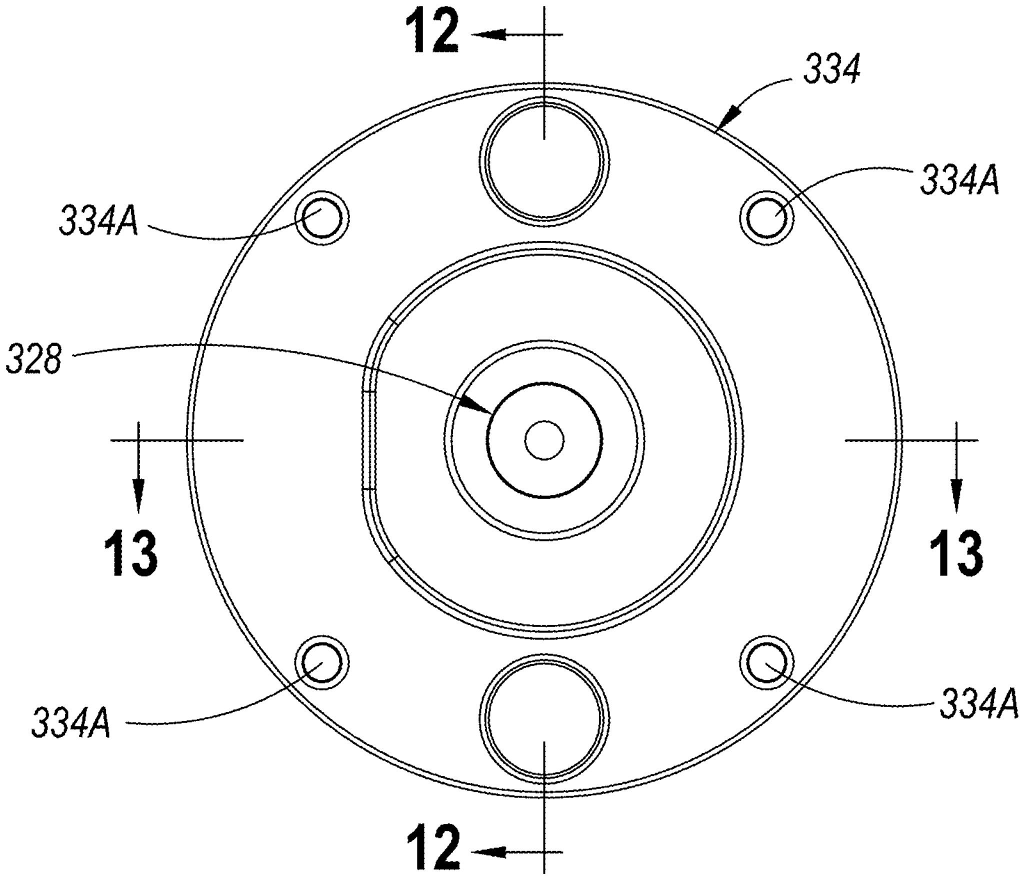
FIG. 11 is an end view of the articulation joint of FIG. 10.

As seen in FIGS. 9A-10, a distal end 306B of the center beam assembly 306 includes a distal retainer 324 that couples the distal end of the articulation joint 300 with a proximal end of the cartridge jaw 202 via one or more fasteners 322, thereby mechanically grounding and retaining the cartridge jaw 202 and thus the end effector 200 relative to the articulation joint 300. The distal retainer 324 includes a plurality of clearance pockets 326 that receive distal ends of articulation cables 402, 404, 406, 408. The distal end 306B further includes a distal retention disc 334 that defines a plurality of cable retention openings 334A. A proximal end 306A of the center beam assembly 306 includes a proximal retainer 332 that couples the proximal end of the articulation joint 300 with a distal end of the shaft assembly 600A.

Figure 12:
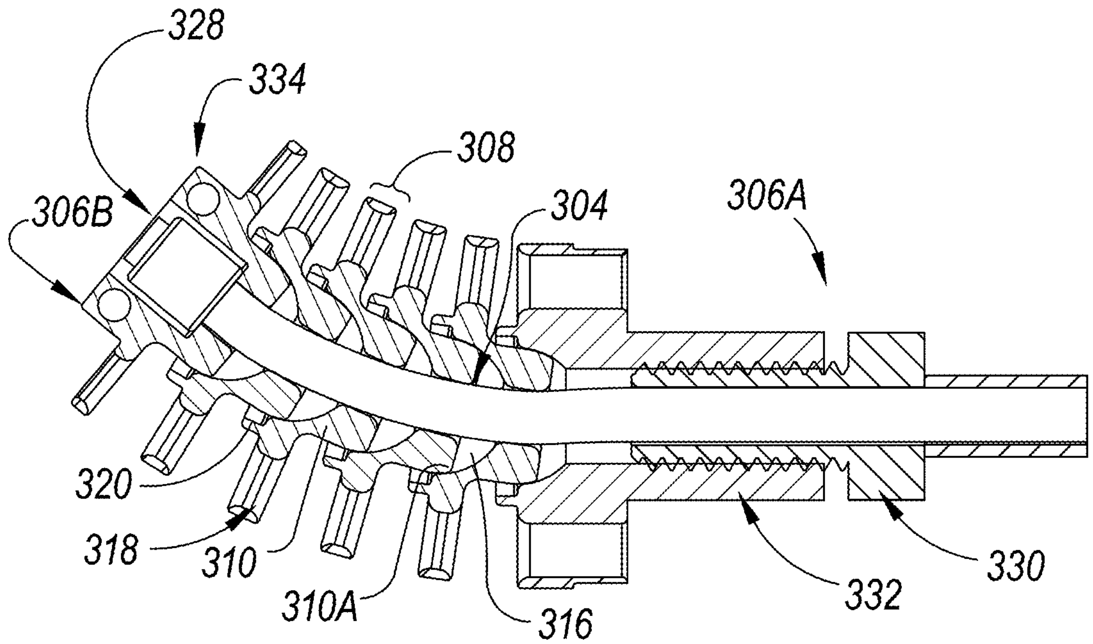
FIG. 12 is a cross-sectional view of a portion of the articulation joint of FIG. 10, taken along line 12-12 in FIG. 11.
Figure 13:
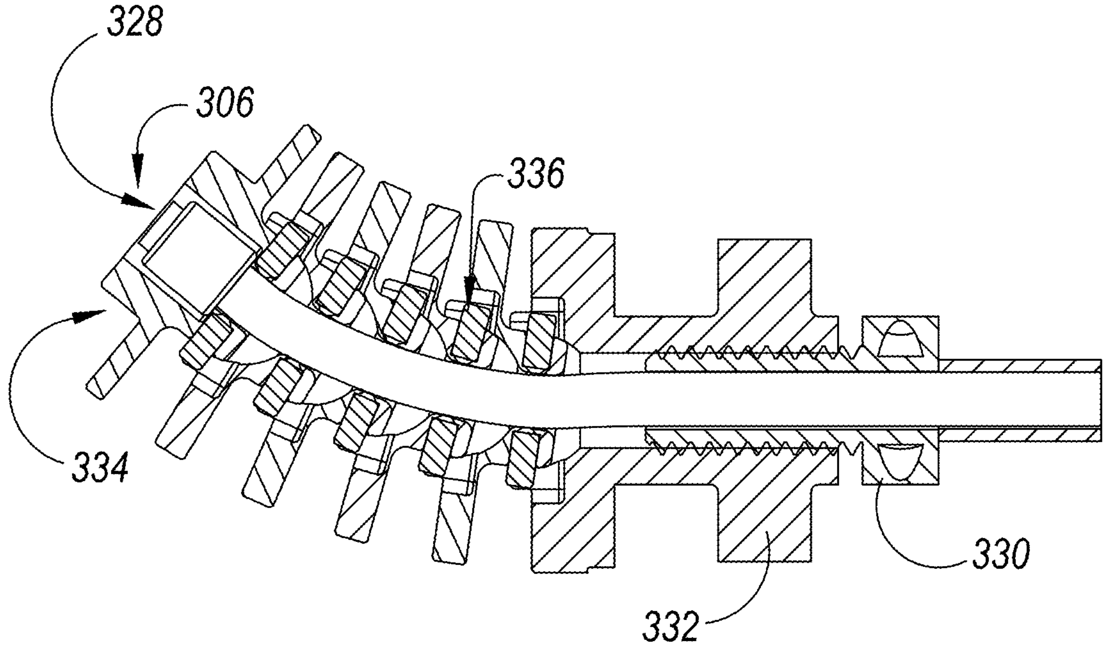
FIG. 13 is a cross-sectional view of a portion of the articulation joint of FIG. 10, taken along line 13-13 in FIG. 11.
Figure 14:
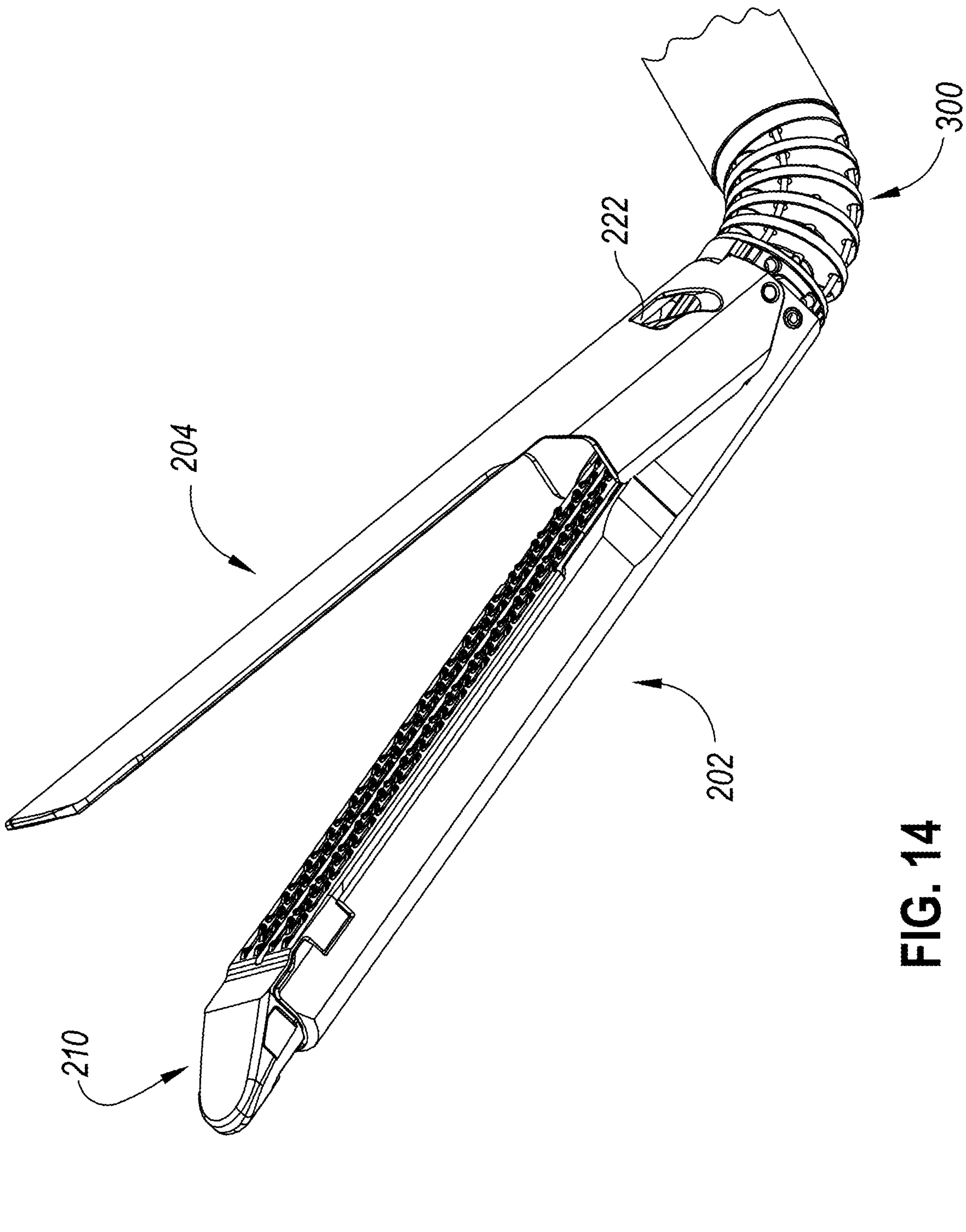
FIG. 14 is a perspective view of the distal end of the surgical instrument of FIG. 1, depicting the end effector articulated vertically and laterally with the anvil open.
Figure 15:
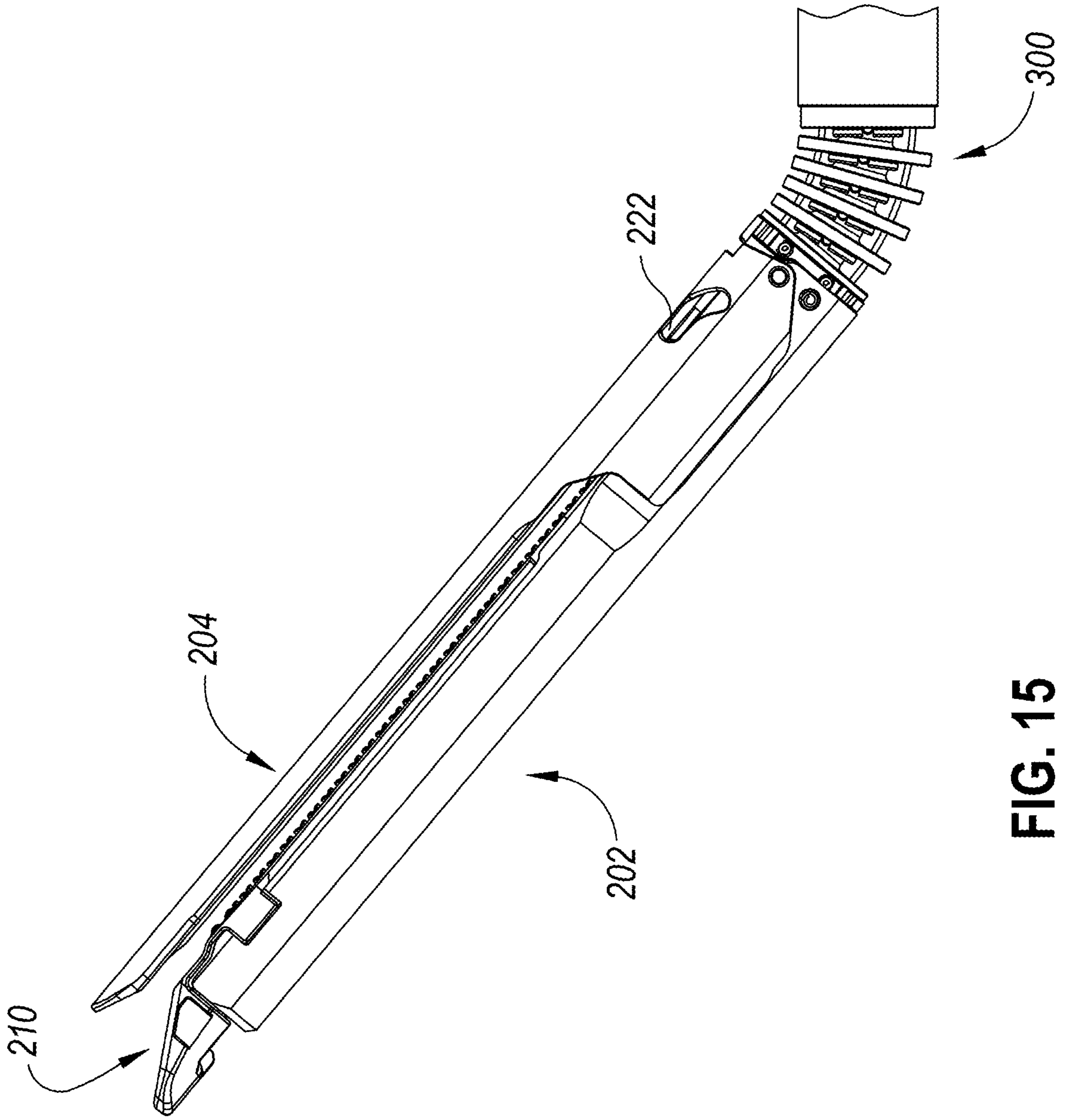
FIG. 15 is a side view of the distal end of the surgical instrument of FIG. 1, depicting the end effector articulated vertically with the anvil closed.
Figure 16:
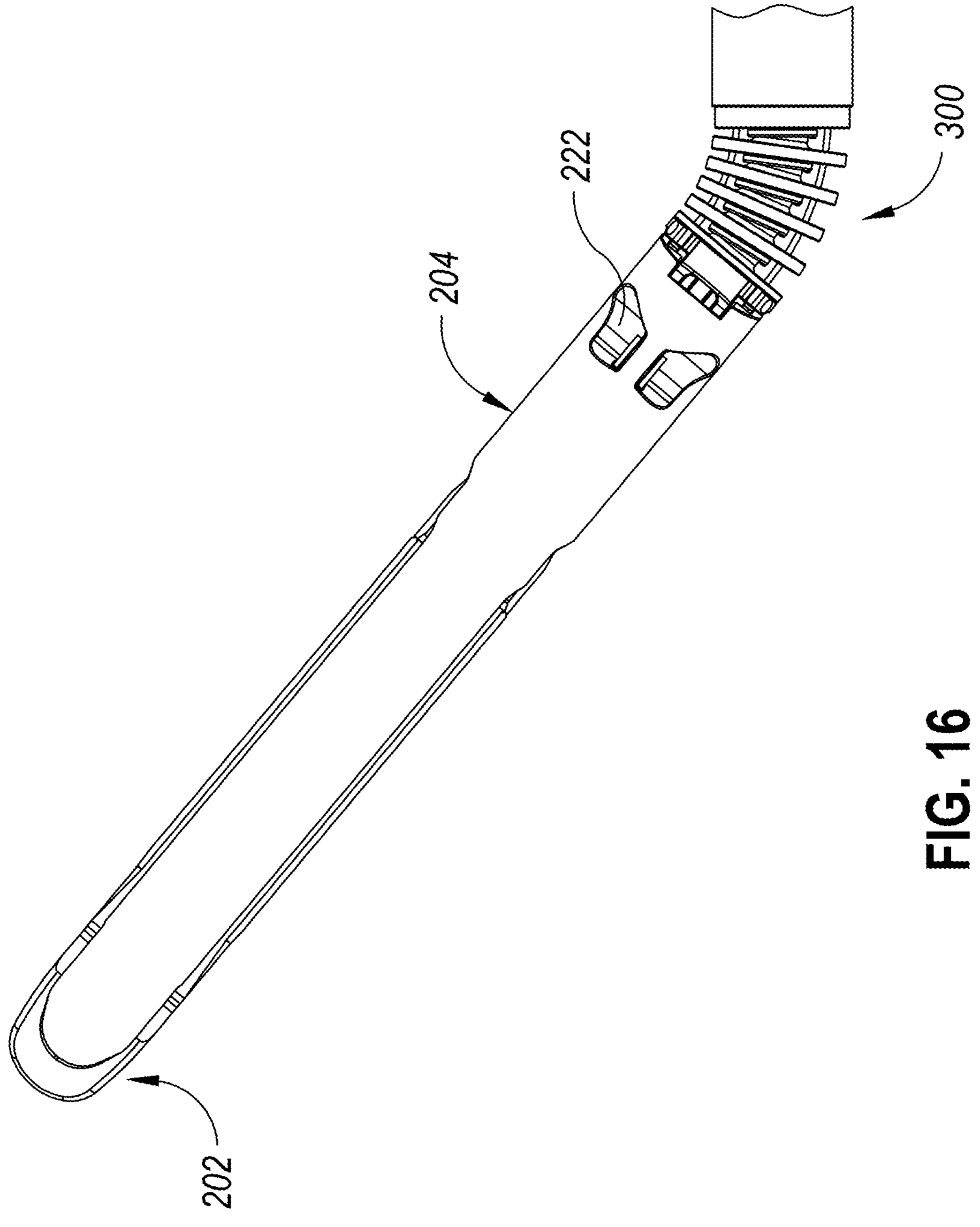
FIG. 16 is a top view of the distal end of the surgical instrument of FIG. 1, depicting the end effector articulated laterally with the anvil closed.

As shown particularly in FIGS. 10, 12, and 13, each joint disc 302 includes an articulation socket 308, an articulation pin 310 protruding outwardly from the articulation socket 308, a first push coil opening 312A defined through the articulation socket 308 and configured to receive a first push coil 508 therethrough, a second push coil opening 312B defined through the articulation socket 308 and configured to receive a second push coil 510 therethrough, and a plurality of articulation cable openings 314A-314D (e.g., a first articulation cable opening 314A, a second articulation cable opening 314B, a third articulation cable opening 314C, and a fourth articulation cable opening 314D) defined through the articulation socket 308 and configured to receive a respective articulation cable 402, 404, 406, 408 (e.g., a first articulation cable 402, a second articulation cable 404, a third articulation cable 406, and a fourth articulation cable 408) therethrough, and discussed in greater detail below. As shown in FIGS. 12 and 13, the central opening 304 is defined in the articulation pin 310 of each joint disc 302. In some versions, three articulation cable openings 314A, 314B, 314C are provided to correspond to three articulation cables 402, 404, 406, while in other versions, four articulation cable openings 314A, 314B, 314C, 314D are provided to correspond to four articulation cables 402, 404, 406, 408.

Each joint disc 302 further includes a rounded articulation pin proximal end 310A and a semi-spherical pin-receiving opening 316 defined in the articulation socket 308. As shown particularly in FIGS. 12 and 13, each rounded articulation pin proximal end 310A pivotally engages in an adjacent pin-receiving opening 316 of an adjacent joint disc 302, with the exception of a proximal-most end 310A that engages with the proximal retainer 332. The articulation pin proximal end 310A and pin-receiving opening 316 interface functions in a similar manner as a swivel bearing. Moreover, the articulation socket 308 includes a socket disc 318 and a pin retention socket 320. A pair of pins 336 are used to provide rotational coupling about a primary axis of the shaft assembly 600A from one disc 302 to the next. In other words, the pins constrain a rotational degree of freedom between adjacent joint discs 302 about the roll axis RA of the instrument 1000. In alternative versions, this feature can be integral to the joint disc 302.

The center beam assembly 306 further includes a center beam 328 that extends longitudinally through the central openings 304 of the joint discs 302. The center beam 328 includes a nitinol core 328A and a stainless-steel collar 328B wound over the nitinol core 328A that allows the center beam 328 to resiliently flex during deflection of the articulation joint 300. The wound stainless-steel collar 328B may have clockwise braiding and counterclockwise braiding to prevent unwinding thereof. The center beam assembly further includes a jack screw 330 that is threadably coupled with the proximal retainer 332 to adjust an axial compression force exerted by the center beam 328 on the array of joint discs 302, thereby enabling adjustment of a pre-load of the articulation joint 300.

The above-described articulation joint 300 forms a portion of the cable articulation subsystem 400 which allows for precise 360-degree movement of the end effector 200 about the articulation joint 300 with at least two degrees of freedom. In some versions, and as dictated by the roll subsystem 600 as well as a need to limit the amount of wrap of the articulation cables 402, 404, 406, 408, the articulation joint 300 is permitted about 320 degrees of roll within the overall system. The cable articulation subsystem 400 also includes a plurality of articulation cables 402, 404, 406, 408 each having a distal end 402A, 404A, 406A, 408A, coupled to the distal end 306B of the center beam assembly 306, and a proximal end 402B, 404B, 406B, 408B. More specifically, each distal end 402A, 404A, 406A, 408A can include a crimp that engages a cable retention opening 334A of the distal retention disc 334 to maintain its positioning. Each articulation cable is discretely manipulable to cause rotation of the articulation joint 300 and end effector 200 about at least one of a pitch axis PA and a yaw axis YA.

In some versions, three articulation cables may be provided rather than the four cables 402, 404, 406, 408 depicted herein. However, four articulation cables 402, 404, 406, 408 circumferentially spaced approximately ninety degrees from one another (as shown) provide load splitting. Additionally, in alternative versions, three and fourth articulation cable configurations may be spaced non-symmetrically relative to one another.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. The housing 700 includes articulation puck assemblies 702, 704, 706, 708 with rotatable capstans (not shown) about which corresponding proximal ends 402B, 404B, 406B, 408B of the articulation cables 402, 404, 406, 408 are windably mounted.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the instrument 1000 (through the inner shaft 604).

The articulation cables 402, 404, 406, 408 are routed and coupled to the end effector 200 via the articulation joint 300 such that movement thereof in a proximal direction (via winding about the capstans of the housing 700) causes the end effector 200 to articulate in a predetermined manner via the articulation joint 300. For example, actuation of the first articulation cable 402 in the proximal direction causes articulation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended articulation of the end effector 200. As will be appreciated by those skilled in the art, this configuration provides for the above-mentioned precise 360-degree articulation of the end effector 200 via the articulation joint 300 with at least two degrees of freedom and about 320 degrees of roll.

As shown throughout FIGS. 2, 4, 5, 8A-8D, 9A-9D, 17 and 19, the knife firing subsystem 500 includes the aforementioned knife 206, the aforementioned knife sled 236, a firing rod 502 that drives the knife 206 and/or knife sled 236, a first push rod 504, and a second push rod 506. The firing rod 502 includes a firing rod rack 530 and is driven by a firing puck assembly 712 of the housing 700. The first push rod 504 has a first push rod distal end 504A coupled to the knife sled 236 and a first push rod proximal end 504B coupled to the firing rod 502. Similarly, the second push rod has a second push rod distal end 506A coupled to the knife sled 236 and a second push rod proximal end 506B coupled to the firing rod 502. The distal ends 504A, 506A are coupled to respective upper and lower portions of the knife sled 236 (e.g., the upper knife tab 238 and the lower knife tab 246), which enables the knife 206 to be pushed evenly at its ends. In some versions, the proximal ends 504B, 506B of the push rods 504, 506 are coupled to the firing rod 502 via a differential 520.

The knife firing subsystem 500 is configured in a manner to enable articulation of the end effector 200 while still enabling proper functionality of the knife 206. To that end, the first push rod 504 includes a first flexible section in the form of a first push coil 508 and the second push rod 506 comprises a second flexible section in the form of a second push coil 510. The push coils 508, 510 route through the articulation joint 300 via the respective push coil openings 312A, 312B, and the push rods 504, 506 engage the respective tab openings 244, 252 in the knife sled 236. A first center cable 512 extends through the first push coil 508 to engage the knife sled 236 via a barrel crimp, and a second center cable 514 extends through the second push coil 510 to engage the knife sled 236 via a barrel crimp. The push coils 508, 510 provide the push rods 504, 506 sufficient stability to deliver an axial firing force to the knife 206, while not being too stiff that would prevent articulation at the joint 300. The cables 512, 514, which are engaged with the knife sled 236 as discussed above (see, e.g., FIG. 8A), prevent the push coils 508, 510 from stretching and/or elongating and serve as retraction cables when the rods 504, 506 are retracted towards the proximal end of the surgical instrument 1000. The entirety of each push rod 504, 506 does not extend through the articulation joint 300, and therefore does not need to be flexible. Accordingly, a proximal section of each push rod 504, 506 can be less flexible than the push coils 508, 510.

II. Illustrative Lockouts for Knife Firing Subsystem

It may be desirable to inhibit firing of the surgical instrument 1000 in instances when the end effector 200 is loaded with a staple cartridge 210 that has already been fired (i.e., a "spent-cartridge" condition), and also when the end effector 200 is not loaded with any staple cartridge at all (i.e., an "absent-cartridge" condition). Attempted firings during such conditions are the result of user error and could result in unintended action on patient tissue; namely, severing the tissue without simultaneously sealing it with staples. The illustrative configuration shown and described below in connection with FIGS. 20-22C is effective to inhibit firing in each of a spent-cartridge condition and an absent-cartridge condition, and thereby protect against such unintended action on patient tissue.

A. Illustrative End Effector with Lockout Assembly

FIGS. 20-22C show an illustrative end effector 1200 that may be readily incorporated into surgical instrument 1000 in replacement of end effector 200 described above. Therefore, end effector 1200 may be substantially similar to end effector 200 described above, with differences elaborated herein. In particular, as will be described in greater detail below, end effector 1200 includes a lockout assembly 1260 configured to inhibit firing of end effector 1200 in the spent-cartridge condition and the absent-cartridge condition.

End effector 1200 includes a cartridge jaw 1202, an anvil jaw 1204, a staple cartridge 1210, a cartridge sled 1210*a*, a knife 1206 defining a knife sled 1236; which may be substantially similar to cartridge jaw 202, anvil jaw 204, staple cartridge 210, cartridge sled 210A, knife 206, and knife sled 236 described above, respectively, with differences elaborated herein. Therefore, cartridge jaw 1202 and anvil jaw 1204 are pivotally coupled to each other and may pivot relative to each other between an open position (similar to end effector 200 shown in FIG. 8A) and a clamping position (similar to end effector 200 shown in FIGS. 8C-8D), in response to movement of knife sled 1236 in accordance with the description herein.

Knife 1206, including its knife sled 1236, are suitably attached to a knife firing subsystem 1500, which is substantially similar to knife firing subsystem 500 described above. Therefore, knife firing subsystem 1500 includes first push rod 1504, a second push rod 1506, push coils 1508, 1510, and center cables 1512, 1514; which may be substantially similar to first push rod 504, second push rod 506, push coils 508, 510, and center cables 512, 514 described above.

Cartridge jaw 1202 includes an elongated channel 1208 and a lower knife channel 1230 having a centrally disposed lower knife channel portion 1232 and at least one lateral lower knife channel wing 1234, which may be substantially similar to elongate channel 208, lower knife channel 230, centrally disposed lower knife channel portion 232, and lateral lower knife channel wings 234 described above, respectively, with differences elaborated below.

Knife sled 1236 includes a vertical column 1235, an upper knife tab 1238 defining an upper knife tab opening 1244, and lower knife tab 1246 defining a lower knife tab opening 1252; which may be substantially similar to vertical column 235, upper knife tab 238, upper knife tab opening 244, lower knife tab 246, and lower knife tab opening 252 described above, respectively, with differences elaborated below. Therefore, upper knife tab 1238 and lower knife tab 1246 may actuate within an upper knife channel of anvil jaw 1204 and lower knife channel 1230 of cartridge jaw 1202, respectively, as knife sled 1236 actuates relative to jaws 1202, 1204 in accordance with the description herein, thereby assisting in pivoting anvil jaw 1204 from the open position into the clamping position.

Staple cartridge 1210 slidably houses cartridge sled 1210*a*. Staple cartridge defines an elongated knife channel 1215 that is substantially similar to elongated knife channel 215 described above, with differences elaborated herein. Elongated channel 1208 of cartridge jaw 1202 may selectively receive a first staple cartridge 1210 such that an unfired staple cartridge 1210 may be loaded into cartridge jaw 1202 and fired in accordance with the description herein. Next, the spent staple cartridge 1210 may be removed from cartridge jaw 1202 such that a new, unfired staple cartridge 1210 may be loaded into cartridge jaw 1202.

As mentioned above, end effector 1200 includes a lockout assembly 1260 configured to inhibit firing of end effector 1200 in both the spent-cartridge condition and the absent-cartridge condition. In the current illustrative example, lockout assembly 1260 includes a rotatable lock 1270, shown in the form of a collar and also referred to as a lock, rotatably attached to knife sled 1236; and a biasing element, shown in the form of a spring 1264. Spring 1264 biases rotatable lock 1270 to rotate relative to knife sled 1236 toward a locked configuration (see FIG. 22A). Cartridge jaw 1202 also defines a recessed pocket 1212 that is formed in the floor of cartridge jaw 1202 and opens laterally to lower knife channel 1230 at a location slightly proximal to a proximal end of a cartridge sled 1210*a* when staple cartridge 1210 in a pre-fired (i.e., unspent) state is suitably loaded within cartridge jaw 1202. Rotatable lock 1270 includes a lockout protrusion 1278 and a lockout cam 1279 each extending radially outwardly from an outer surface of rotatable lock 1270, where lockout protrusion 1278 and lockout cam 1279 are circumferentially spaced apart from one another. Lockout protrusion 1278 is sized to fit inside recessed pocket 1212 and thus engage the floor of cartridge jaw 1202 to thereby inhibit longitudinal translation of knife sled 1236 when rotatable lock 1270 is in the locked configuration. Lockout cam 1279 includes an upwardly facing cam surface along a distal portion of rotatable lock 1270 that faces towards anvil jaw 1204 and is configured to facilitate cartridge sled 1210*a* in rotatably driving rotatable lock 1270 from the locked configuration to the unlocked configuration, as described below.

As will be described in greater detail below, while a non-fired staple cartridge 1210 is being suitably loaded into cartridge jaw 1202, the upwardly facing cam surface of lockout cam 1279 of rotatable lock 1270 is configured to engage a lower surface of the non-fired cartridge sled 1210*a*. Such engagement with the lower surface will thereby rotate lockout body 1270 relative to knife sled 1236 such that lockout protrusion 1278 rotates out of recessed pocket 1212 defined by cartridge jaw 1202, thus transitioning rotatable lock 1270 from the locked configuration toward the unlocked configuration. As will also be described in greater detail below, if a spent staple cartridge 1210 is loaded into cartridge jaw 1202 (i.e., a spent-cartridge condition), or if a staple cartridge 1210 is absent from cartridge jaw 1202 (i.e., an absent-cartridge condition), spring 1264 will drive rotatable lock 1270 relative to knife sled 1236 into recessed pocket 1212, thereby establishing the locked configuration and inhibiting distal actuation of knife 1206.

Spring 1264 is interposed between a proximally facing surface 1277 of rotatable lock 1270 and a distally facing surface 1237 of lower knife tab 1246 of knife sled 1236. As described below, a first portion of spring 1264 is longitudinally affixed to rotatable lock 1270, and a second portion of spring 1264 is longitudinally affixed to knife sled 1236. Consequently, rotatable lock 1270 and spring 1264 advance longitudinally with knife 1206 and knife sled 1236 as knife 1206 advances longitudinally relative to end effector jaws 1202, 1204. Lower knife tab 1246 includes a cylindrical lug projecting distally therefrom and defining a rotation axis RA and extends along (for example, substantially parallel to) a longitudinal axis of end effector 1200. Rotatable lock 1270 and spring 1264 are positioned around lug 1247 to where rotatable lock 1270 and a portion of spring 1264 are rotatable around lug 1247 about the rotation axis RA.

Figure 22A:
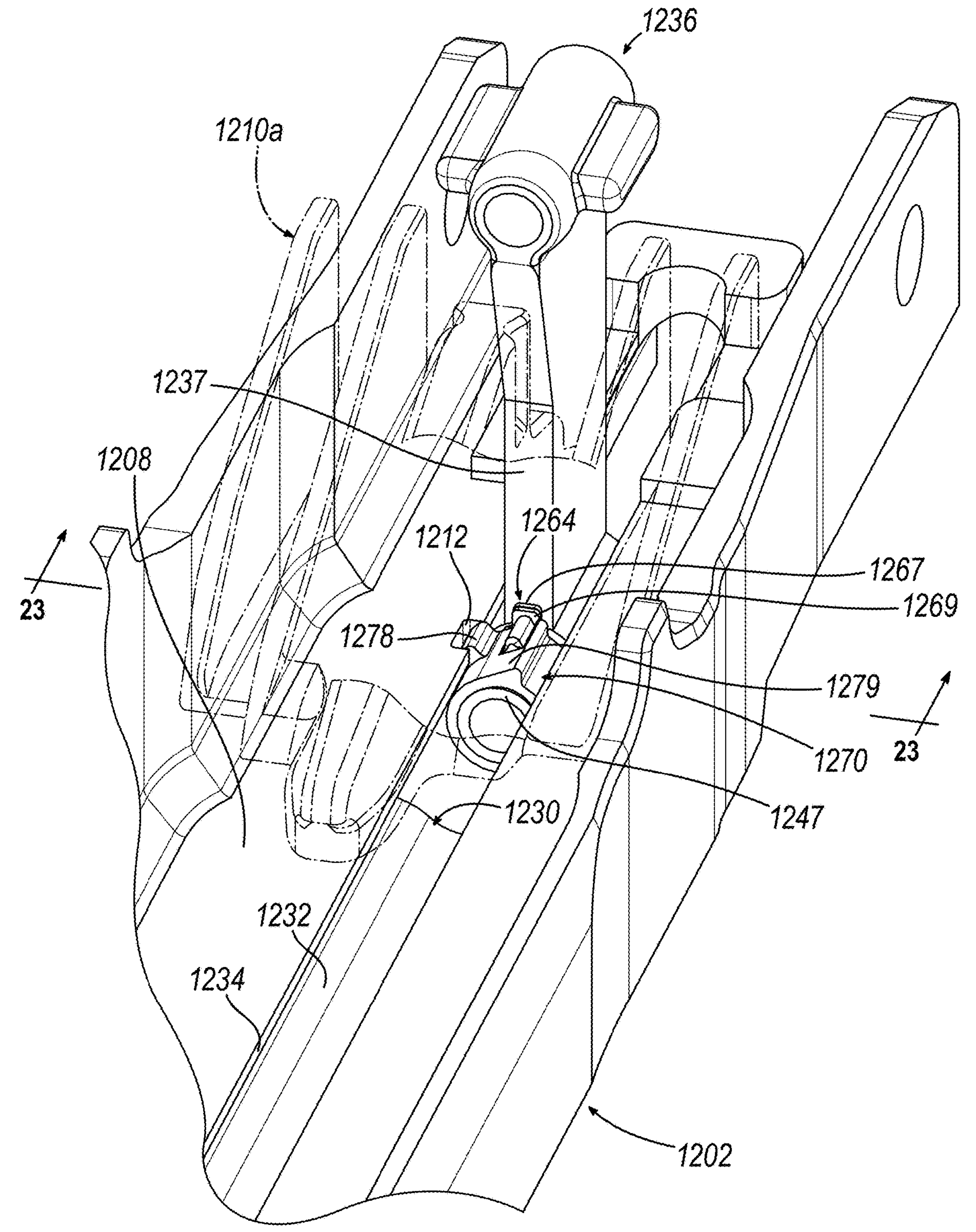
FIG. 22A is a perspective view of the knife lockout assembly of FIG. 20 in a locked configuration.

Spring 1264 rotationally biases rotatable lock 1270 relative to lower knife tab 1246 of knife sled 1236, thereby biasing rotatable lock 1270 toward the locked configuration (see FIG. 22A). While a spring 1264 is used in the current example, any other suitable biasing element may be utilized in order to bias rotatable lock 1270 toward the locked configuration as would be apparent to one skilled in the art in view of the teachings herein. For example, a compression spring may be utilized to bias rotatable lock 1270. Such alternative biasing elements may have any suitable spatial relationship with other components of lockout assembly 1260 and end effector 1200 as would be apparent to one skilled in the art in view of the teachings herein.

For spring 1264 to bias rotatable lock 1270 in the current version, distally facing surface 1237 includes a distal projection 1239, depicted as a pin. Distal projection 1239 fits inside of a proximal opening 1266 on a proximal tab 1267 of spring 1264, for example with a press-fit, to thereby inhibit rotation of proximal tab 1267 of spring 1264 relative to knife sled 1236. Meanwhile, spring 1264 also defines a distal opening 1268 positioned on a distal tab 1269 of spring 1264. Collar 1270 includes a proximal projection 1272, depicted as a pin, extending from proximally facing surface 1277 and sized to fit inside of distal opening 1268, for example with a press-fit. In this manner, proximal spring tab 1267 is rotationally fixed relative to knife sled 1236 about rotation axis RA, and distal spring tab 1269 is rotationally fixed relative to rotatable lock 1270 about rotation axis RA. As noted above, rotatable lock 1270 remains rotatable about knife sled lug 1247 and rotation axis RA between the locked and unlocked configurations. Consequently, spring tabs 1267 and spring openings 1266, 1268 are circumferentially aligned with one another in the locked configuration (see FIG. 22A) and are circumferentially offset from one another in the unlocked configuration (see FIGS. 22B-22C).

Figure 22B:
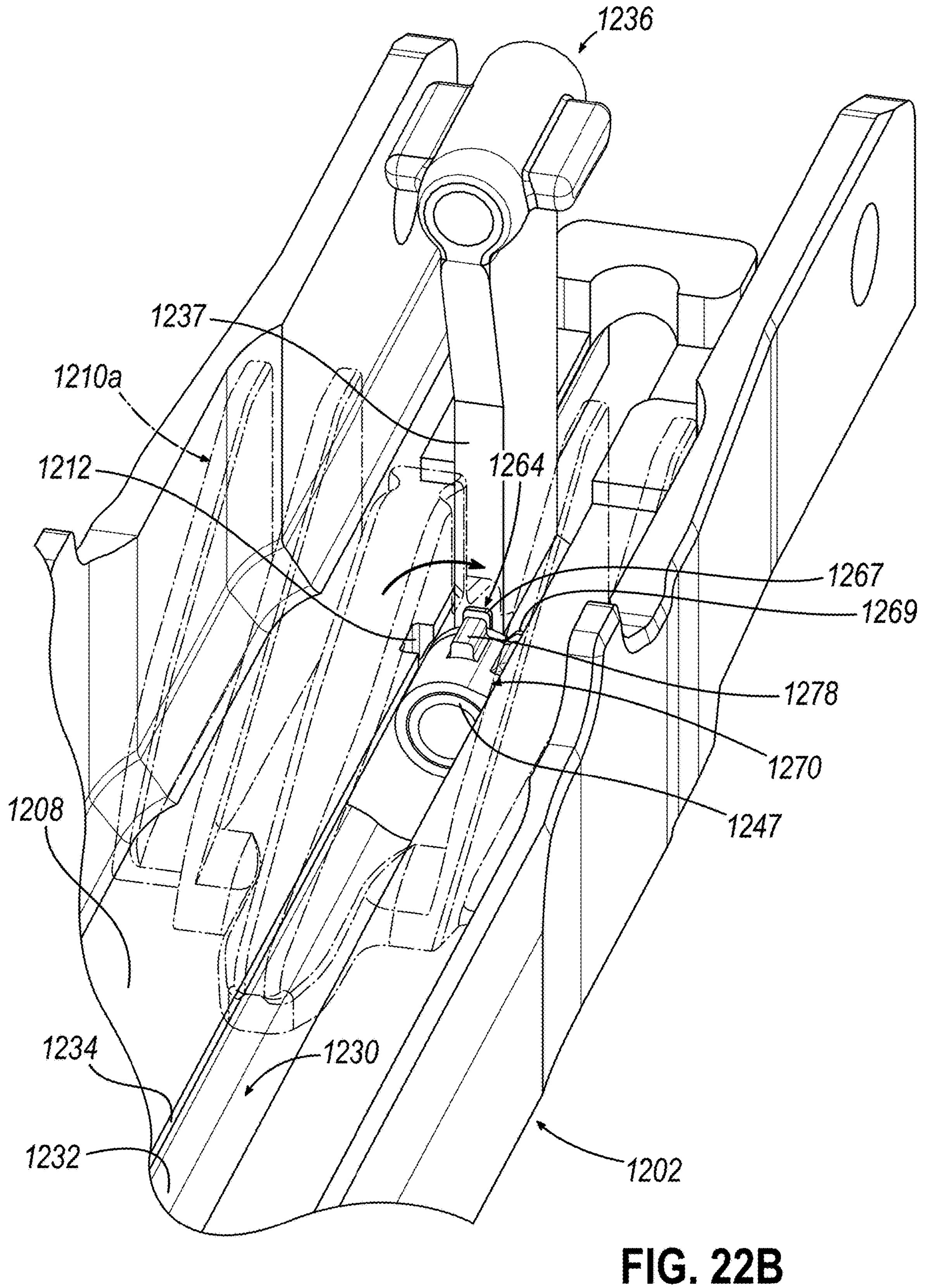
FIG. 22B is a perspective view of the knife lockout assembly of FIG. 20 in an unlocked configuration.
Figure 22C:
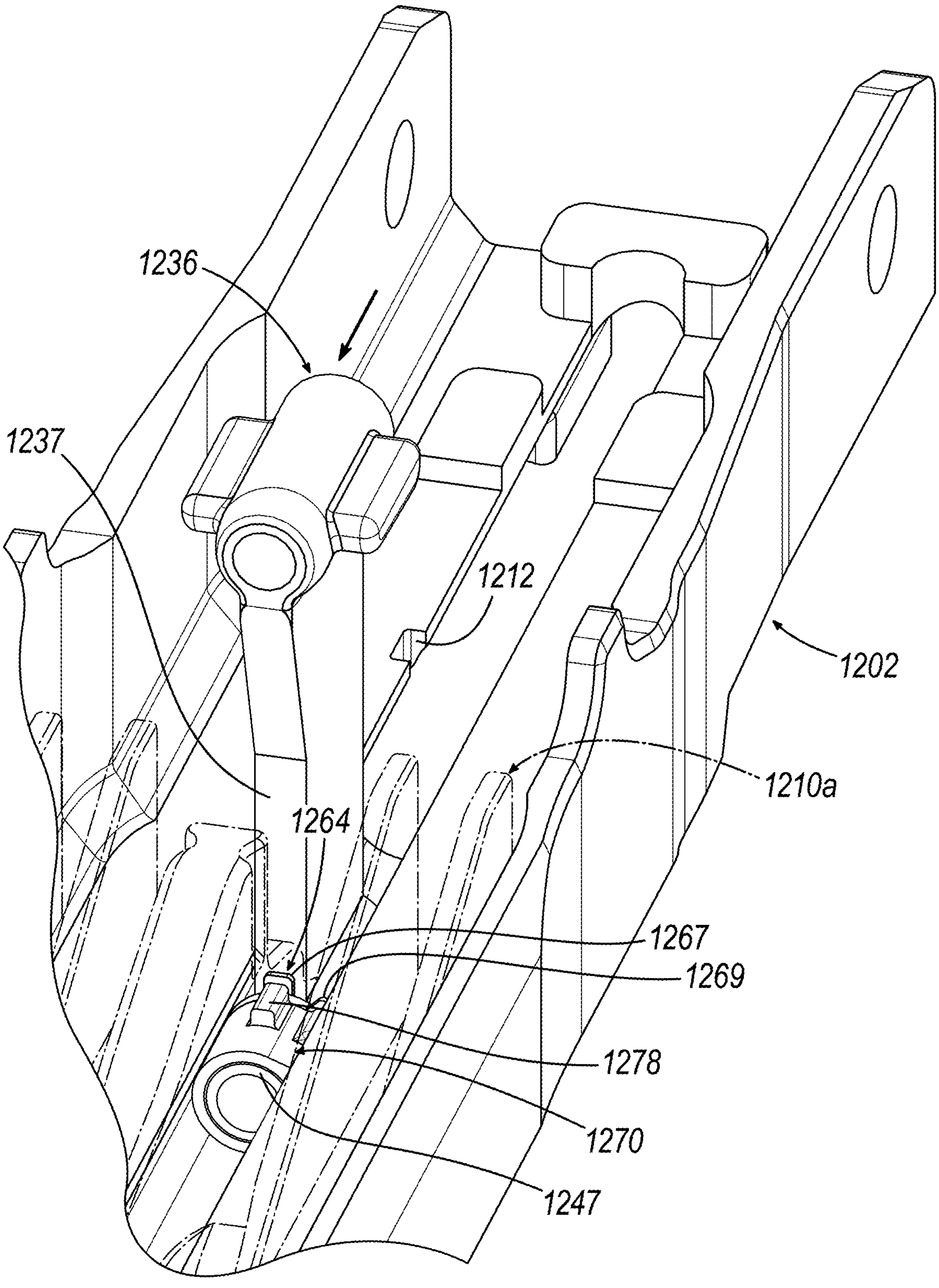
FIG. 22C is a perspective view of the knife and knife lockout assembly of FIG. 20 in an unlocked configuration and at a distally advanced position.
Figure 23A:
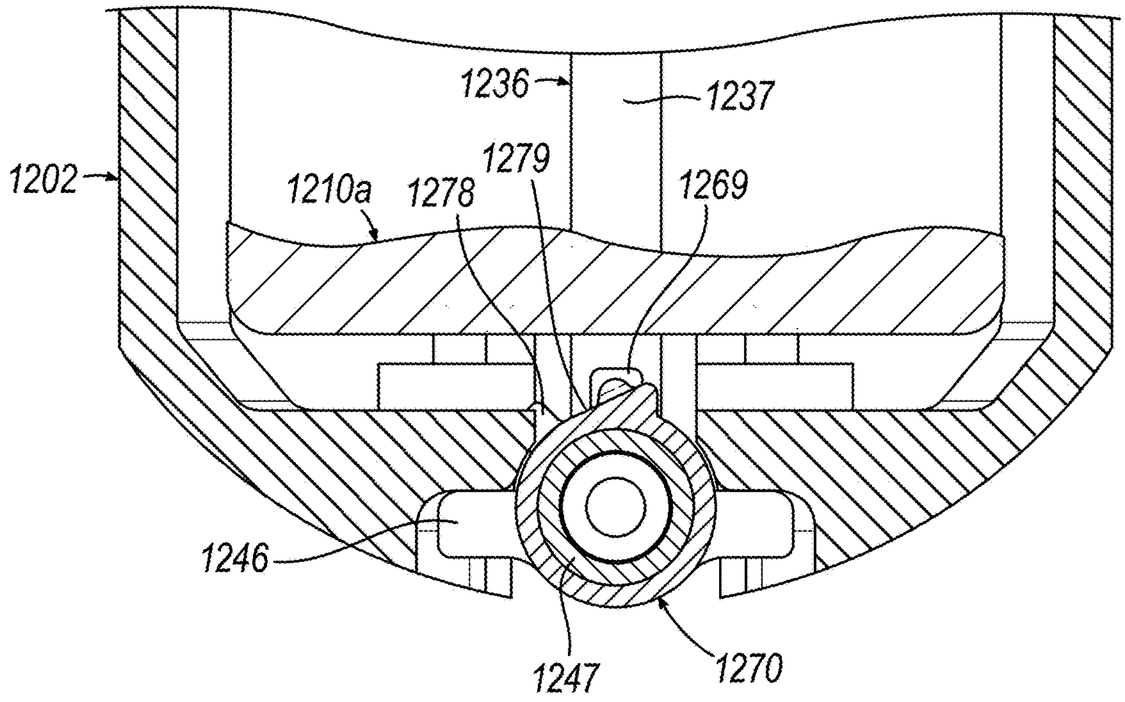
FIG. 23A is a front view of the knife lockout assembly, oriented in the locked configuration as shown in FIG. 22A, taken along line 23-23 of FIG. 22A.

FIGS. 22A-22C and 23A-23B show an illustrative firing of knife sled 1236 when an unfired staple cartridge 1210 is suitably loaded into end effector 1200. As shown in FIGS. 22A and 23A, cartridge sled 1210*a* is located distally relative to recessed pocket 1212 of cartridge jaw 1202. Further, knife 1206, knife sled 1236, spring 1264, and rotatable lock 1270 are all located proximally relative to cartridge sled 1210*a*. Rotatable lock 1270 is in the pre-fired, locked configuration. Therefore, spring 1264 biases rotatable lock 1270 such that lockout protrusion 1278 is positioned within recessed pocket and engages cartridge jaw 1202 to inhibit distal advancement of knife 1206. It should be understood that as knife 1206 actuates distally from the proximal position (see FIG. 22A-22B) in a distal direction (see FIG. 22C), lower knife tab 1246 may ride against the lower surface of lower knife channel 1230.

Figure 23B:
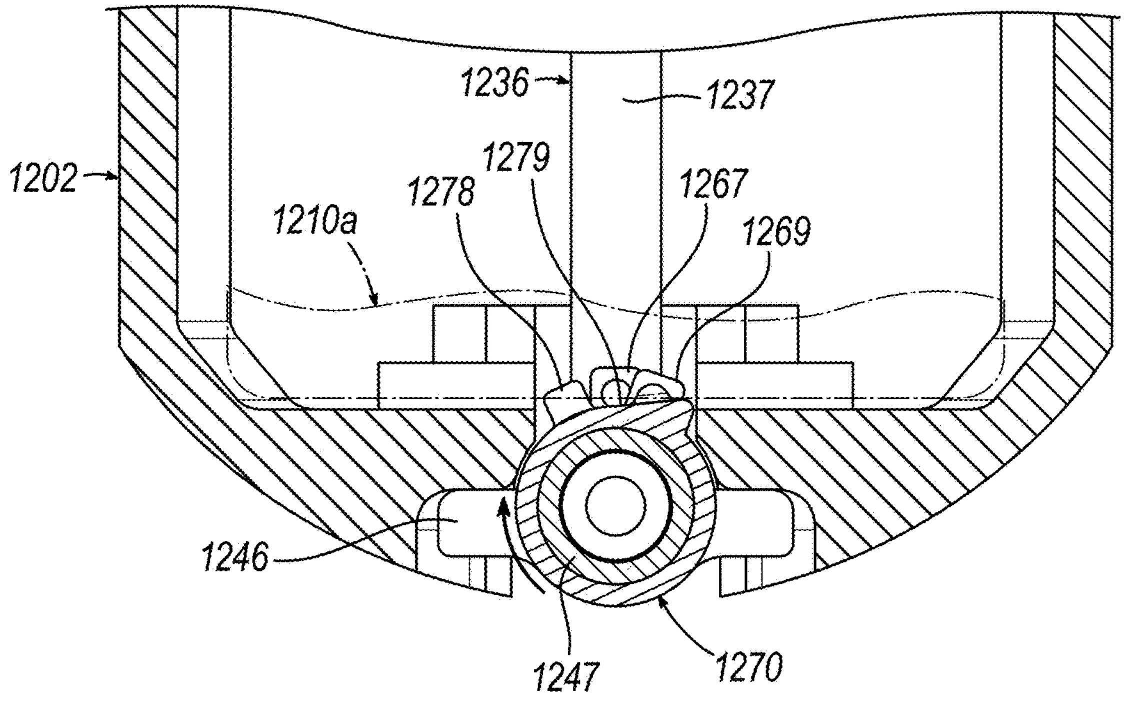
FIG. 23B is a front view of the knife lockout assembly, oriented in the unlocked configuration as shown in FIG. 22B, taken along line 23-23 of FIG. 22A.

FIGS. 22B and 23B show an underside of cartridge sled 1210*a* of an unspent staple cartridge 1210 pressing downwardly against lockout cam 1279 to thereby rotate rotatable lock 1270 about the rotation axis RA from the locked configuration to unlocked configuration. As discussed above, lockout protrusion 1278 in the unlocked configuration is positioned outside of recessed pocket 1212 so as to permit knife 1206 to advance distally through a firing stroke. As can be seen, proximal spring tab 1267 remains coupled to knife sled 1236 while distal spring tab 1269 remains coupled to rotatable lock 1270 such that spring 1264 continues to exert a rotational bias force on rotatable lock 1270 in a direction toward the locked configuration.

Next, as shown in FIG. 22C, with rotatable lock 1270 in the unlocked configuration, knife 1206 and cartridge sled 1210*a* may be advanced distally, effectively passing the recessed pocket 1212 of cartridge jaw 1202 so that staple cartridge 1210 may be fired on tissue clamped between end effector jaws 1202, 1204. Cartridge sled 1210*a* continues to exert a downward force on lockout cam 1279 through the distal firing stroke, thus maintaining rotatable lock 1270 in the unlocked configuration.

FIG. 23A shows a front facing end view of rotatable lock 1270 in the locked configuration and positioned around cylindrical lug 1247, similar to that depicted in FIG. 22A. While in the locked configuration, rotatable lock 1270 can be seen biased counterclockwise by spring 1264 such that lockout protrusion 1278 is inside of recessed pocket 1212. Cartridge sled 1210*a* is shown elevated above lockout cam 1279.

FIG. 23B shows the front facing end view of rotatable lock 1270 in the unlocked configuration, similar to that depicted in FIG. 22B. Here, a lower surface of cartridge sled 1210*a* has contacted lockout cam 1279 to thus rotate rotatable lock 1270 in the arrow direction such that lockout protrusion 1278 is out of recessed pocket 1212. The force applied on lockout cam 1279 by cartridge sled 1210*a* is enough to overcome the biasing force of spring 1264 and thus drives distal tab 1269 of spring 1264 to move with rotatable lock 1270. During rotation of rotatable lock 1270, the lower surface of cartridge sled 1210*a* slides against lockout cam 1279. As described above, knife sled 1236 is capable of translating distally when rotatable lock 1270 is in the unlocked configuration, as shown in FIG. 22C.

Following completion of the distal firing stroke, knife 1206 is retracted proximally while cartridge sled 1210*a* remains positioned at the distal end of staple cartridge 1210, such that cartridge sled 1210*a* no longer engages rotatable lock 1270. As a result, when knife 1206 resumes its proximal home position in which lockout protrusion 1278 longitudinally aligns with recessed pocket 1212, the resilient bias force exerted by spring 1264 rotates lockout protrusion 1278 into recessed pocket 1212 such that rotatable lock 1270 resumes the locked configuration, as shown in FIG. 22A. Rotatable lock 1270 then maintains this locked configuration until a new, unspent staple cartridge is loaded into end effector 1200. In this manner, lockout assembly 1260 continues to inhibit firing of end effector 1200 in each of a spent-cartridge condition and an absent-cartridge condition.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: a first jaw (202) configured to selectively receive a staple cartridge (210) and defining a longitudinal jaw axis; a second jaw (204), wherein the first and second jaws are configured to cooperate to clamp and staple tissue; a knife (1236) configured to actuate relative to the first jaw and the second jaw along the longitudinal jaw axis while the staple cartridge is housed within the first jaw to thereby cut and staple tissue clamped by the first and second jaws, wherein the knife defines a longitudinal knife axis that extends along the longitudinal jaw axis; and a lock (1270) rotatable relative to the knife about the longitudinal knife axis between an unlocked configuration and a locked configuration, wherein the lock is configured to inhibit distal actuation of the knife in the locked configuration and permit distal actuation of the knife in the unlocked configuration, wherein the lock is configured to assume the locked configuration in an absence of an unspent staple cartridge in the first jaw and to assume the unlocked configuration in a presence of an unspent staple cartridge in the first jaw.

Example 2

The apparatus of example 1, wherein the apparatus further comprises a spring (1264), wherein the lock includes a collar (1270), wherein the collar is longitudinally affixed to the knife, wherein the spring is affixed to the collar and is configured to bias the lock towards the locked configuration.

Example 3

The apparatus of example 2, wherein the spring comprises one of a snap-ring, a spring ring, a split-ring or a torsion spring.

Example 4

The apparatus of any of examples 2-3, wherein the collar and spring are axially aligned with each other.

Example 5

The apparatus of any of examples 1-4, wherein the knife includes a lug (1247), wherein the lug defines the longitudinal knife axis, wherein the lock is rotatable about the lug between the locked and unlocked configurations.

Example 6

The apparatus of any of examples 1-5, wherein the lug is positioned at a lower end of the knife and projects distally.

Example 7

The apparatus of any of examples 1 and 5-6, wherein the apparatus further comprises a spring configured to bias the lock towards the locked configuration, wherein the spring is positioned about the lug.

Example 8

The apparatus of any of examples 1-7, the first jaw including a floor having an elongate slot (1208) extending along the longitudinal jaw axis and through which the knife is configured to translate, where a recess (1212) is formed in the floor and opens laterally to the elongate slot.

Example 9

The apparatus of any of examples 1-8, wherein the lock includes a protrusion (1278), wherein the first jaw includes a recess (1212), wherein the protrusion is configured to be positioned inside of the recess and thus constrained longitudinally by the recess when the lock is in the locked configuration, wherein the protrusion is configured to be positioned outside of the recess and thus unconstrained longitudinally by the recess when the lock is in the unlocked configuration.

Example 10

The apparatus of any of examples 1-9, wherein the lock includes a cam surface (1279) configured to engage the staple cartridge to thereby transition the lock from the locked configuration to the unlocked configuration.

Example 11

The apparatus of any of examples 1, 5-6, and 8-10, wherein the lock includes a pin (1272) extending in a proximal direction towards the knife, wherein the pin is configured to engage a spring to thereby bias the lock towards the locked configuration.

Example 12

The apparatus of example 10, wherein the lock includes a protrusion (1278), wherein the first jaw includes a recess (1212), wherein the protrusion is configured to be positioned inside of the recess and thus constrained longitudinally by the recess when the lock is in the locked configuration, wherein the cam surface and the protrusion are circumferentially offset from one another.

Example 13

The apparatus of any of examples 10-12, wherein the cam surface is defined by a distal portion of the lock.

Example 14

The apparatus of any of examples 1-13, wherein the lock is longitudinally secured to the knife such that the lock is translatable longitudinally with the knife relative to the first and second jaws.

Example 15

The apparatus of any of examples 1-14, wherein the knife is actuatable from a proximal home position to a distal fired position when the lock is in the unlocked configuration, wherein the lock is configured to automatically resume the locked configuration in response to the knife returning to the proximal home position from the distal fired position.

Example 16

An apparatus comprising: a first jaw configured to selectively receive a staple cartridge and defining a longitudinal jaw axis; a second jaw, wherein the first and second jaws are configured to cooperate to clamp and staple tissue; a knife configured to actuate relative to the first jaw and the second jaw along the longitudinal jaw axis while the staple cartridge is housed within the first jaw to thereby cut and staple tissue clamped by the first and second jaws, wherein the knife defines a longitudinal knife axis that extends along the longitudinal jaw axis; and a lock configured to rotate about the longitudinal knife axis relative to the knife between an unlocked configuration and a locked configuration, wherein the lock is configured to inhibit distal actuation of the knife in the locked configuration and permit distal translation of the knife in the unlocked configuration, the lock including a collar and a spring positioned between the collar and the knife, wherein the spring is configured to bias the collar towards the locked configuration.

Example 17

The apparatus of example 16, wherein the knife includes a lug, wherein the lug defines the longitudinal knife axis, wherein the lock is rotatable about the lug between the locked and unlocked configurations.

Example 18

The apparatus of any of examples 16-17, wherein the lock includes a protrusion, wherein the first jaw includes a recess, wherein the protrusion is configured to be positioned inside of the recess and thus constrained longitudinally by the recess when the lock is in the locked configuration, wherein the protrusion is configured to be positioned outside of the recess and thus unconstrained longitudinally by the recess when the lock is in the unlocked configuration.

Example 19

An apparatus comprising: a staple cartridge; and an end effector operable to clamp, staple, and cut tissue, comprising: a first jaw configured to selectively receive the staple cartridge, a second jaw, wherein the first jaw and the second jaw are configured to transition between an open position and a closed position to clamp tissue, a knife configured to actuate distally relative to the first jaw and the second jaw along a firing stroke while the staple cartridge is housed within the first jaw to thereby cut and staple tissue clamped by the first and second jaws, the knife including a lug protruding longitudinally in a distal direction, and a lock configured to rotate about the lug of the knife between an unlocked configuration and a locked configuration, wherein the lock is configured to inhibit distal actuation of the knife in the locked configuration and permit distal translation of the knife in the unlocked configuration, wherein the lock is configured to engage the staple cartridge to thereby rotate about the lug and to thus transition from the locked configuration to the unlocked configuration.

Example 20

The apparatus of example 20, wherein the staple cartridge includes a sled configured to directly contact and thereby drive the lock from the locked configuration to the unlocked configuration when the staple cartridge in an unspent state is fully seated within the first jaw.

Clause 1

An apparatus comprising: a first jaw configured to selectively receive a staple cartridge and defining a longitudinal jaw axis; a second jaw, wherein the first and second jaws are configured to cooperate to clamp and staple tissue; a knife configured to actuate relative to the first jaw and the second jaw along the longitudinal jaw axis while the staple cartridge is housed within the first jaw to thereby cut and staple tissue clamped by the first and second jaws, wherein the knife defines a longitudinal knife axis that extends along the longitudinal jaw axis; and a lock rotatable relative to the knife about the longitudinal knife axis between an unlocked configuration and a locked configuration, wherein the lock is configured to inhibit distal actuation of the knife in the locked configuration and permit distal actuation of the knife in the unlocked configuration, wherein the lock is configured to assume the locked configuration in an absence of an unspent staple cartridge in the first jaw and to assume the unlocked configuration in a presence of an unspent staple cartridge in the first jaw.

Clause 2

The apparatus of clause 1, wherein the apparatus further comprises a spring, wherein the lock includes a collar, wherein the collar is longitudinally affixed to the knife, wherein the spring is affixed to the collar and is configured to bias the lock towards the locked configuration.

Clause 3

The apparatus of clause 2, wherein the spring comprises one of a snap-ring, a spring ring, a split-ring or a torsion spring.

Clause 4

The apparatus of clause 3, wherein the collar and spring are axially aligned with each other.

Clause 5

The apparatus of clause 1, wherein the knife includes a lug, wherein the lug defines the longitudinal knife axis, wherein the lock is rotatable about the lug between the locked and unlocked configurations.

Clause 6

The apparatus of clause 5, wherein the lug is positioned at a lower end of the knife and projects distally.

Clause 7

The apparatus of clause 5, wherein the apparatus further comprises a spring configured to bias the lock towards the locked configuration, wherein the spring is positioned about the lug.

Clause 8

The apparatus of clause 1, the first jaw including a floor having an elongate slot extending along the longitudinal jaw axis and through which the knife is configured to translate, where a recess is formed in the floor and opens laterally to the elongate slot.

Clause 9

The apparatus of clause 1, wherein the lock includes a protrusion, wherein the first jaw includes a recess, wherein the protrusion is configured to be positioned inside of the recess and thus constrained longitudinally by the recess when the lock is in the locked configuration, wherein the protrusion is configured to be positioned outside of the recess and thus unconstrained longitudinally by the recess when the lock is in the unlocked configuration.

Clause 10

The apparatus of clause 1, wherein the lock includes a cam surface configured to engage the staple cartridge to thereby transition the lock from the locked configuration to the unlocked configuration.

Clause 11

The apparatus of clause 10, wherein the lock includes a pin extending in a proximal direction towards the knife, wherein the pin is configured to engage a spring to thereby bias the lock towards the locked configuration.

Clause 12

The apparatus of clause 10, wherein the lock includes a protrusion, wherein the first jaw includes a recess, wherein the protrusion is configured to be positioned inside of the recess and thus constrained longitudinally by the recess when the lock is in the locked configuration, wherein the cam surface and the protrusion are circumferentially offset from one another.

Clause 13

The apparatus of clause 10, wherein the cam surface is defined by a distal portion of the lock.

Clause 14

The apparatus of clause 1, wherein the lock is longitudinally secured to the knife such that the lock is translatable longitudinally with the knife relative to the first and second jaws.

Clause 15

The apparatus of clause 1, wherein the knife is actuatable from a proximal home position to a distal fired position when the lock is in the unlocked configuration, wherein the lock is configured to automatically resume the locked configuration in response to the knife returning to the proximal home position from the distal fired position.

Clause 16

An apparatus comprising: a first jaw configured to selectively receive a staple cartridge and defining a longitudinal jaw axis; a second jaw, wherein the first and second jaws are configured to cooperate to clamp and staple tissue; a knife configured to actuate relative to the first jaw and the second jaw along the longitudinal jaw axis while the staple cartridge is housed within the first jaw to thereby cut and staple tissue clamped by the first and second jaws, wherein the knife defines a longitudinal knife axis that extends along the longitudinal jaw axis; and a lock configured to rotate about the longitudinal knife axis relative to the knife between an unlocked configuration and a locked configuration, wherein the lock is configured to inhibit distal actuation of the knife in the locked configuration and permit distal translation of the knife in the unlocked configuration, the lock including a collar and a spring positioned between the collar and the knife, wherein the spring is configured to bias the collar towards the locked configuration.

Clause 17

The apparatus of clause 17, wherein the knife includes a lug, wherein the lug defines the longitudinal knife axis, wherein the lock is rotatable about the lug between the locked and unlocked configurations.

Clause 18

The apparatus of clause 16, wherein the lock includes a protrusion, wherein the first jaw includes a recess, wherein the protrusion is configured to be positioned inside of the recess and thus constrained longitudinally by the recess when the lock is in the locked configuration, wherein the protrusion is configured to be positioned outside of the recess and thus unconstrained longitudinally by the recess when the lock is in the unlocked configuration.

Clause 19

An apparatus comprising: a staple cartridge; and an end effector operable to clamp, staple, and cut tissue, comprising: a first jaw configured to selectively receive the staple cartridge, a second jaw, wherein the first jaw and the second jaw are configured to transition between an open position and a closed position to clamp tissue, a knife configured to actuate distally relative to the first jaw and the second jaw along a firing stroke while the staple cartridge is housed within the first jaw to thereby cut and staple tissue clamped by the first and second jaws, the knife including a lug protruding longitudinally in a distal direction, and a lock configured to rotate about the lug of the knife between an unlocked configuration and a locked configuration, wherein the lock is configured to inhibit distal actuation of the knife in the locked configuration and permit distal translation of the knife in the unlocked configuration, wherein the lock is configured to engage the staple cartridge to thereby rotate about the lug and to thus transition from the locked configuration to the unlocked configuration.

Clause 20

The apparatus of clause 19, wherein the staple cartridge includes a sled configured to directly contact and thereby drive the lock from the locked configuration to the unlocked configuration when the staple cartridge in an unspent state is fully seated within the first jaw.

IV. Miscellaneous

It should be understood that any one or more of the teachings, expressions, versions, examples, etc. described herein may be combined with any one or more of the other teachings, expressions, versions, examples, etc. that are described herein. The above-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a first jaw configured to selectively receive a staple cartridge and defining a central plane and a longitudinal jaw axis;
(b) a second jaw, wherein the first and second jaws are configured to cooperate to clamp and staple tissue;
(c) a knife having a knife edge and being configured to actuate relative to the first jaw and the second jaw along the longitudinal jaw axis while the staple cartridge is housed within the first jaw to thereby cut and staple tissue clamped by the first and second jaws, wherein the knife defines a longitudinal knife axis that extends along the longitudinal jaw axis, wherein each of the longitudinal jaw axis, the knife edge, and the longitudinal knife axis extends along the central plane; and
(d) a lock rotatable relative to the knife about the longitudinal knife axis between an unlocked configuration and a locked configuration, wherein the lock includes a cam surface extending through the central plane,
wherein the lock is configured to inhibit distal actuation of the knife in the locked configuration and permit distal actuation of the knife in the unlocked configuration,
wherein the lock is configured to assume the locked configuration in an absence of an unspent staple cartridge in the first jaw and to assume the unlocked configuration in a presence of an unspent staple cartridge in the first jaw via an engagement between the cam surface with the unspent staple cartridge,
wherein the cam surface is configured to engage the staple cartridge to thereby transition the lock from the locked configuration to the unlocked configuration.

2. The apparatus of claim 1, wherein the apparatus further comprises a spring, wherein the lock includes a collar, wherein the collar is longitudinally affixed to the knife, wherein the spring is affixed to the collar and is configured to bias the lock towards the locked configuration.

3. The apparatus of claim 2, wherein the spring comprises one of a snap-ring, a spring ring, a split-ring or a torsion spring.

4. The apparatus of claim 3, wherein the collar and spring are axially aligned with each other.

5. The apparatus of claim 1, wherein the knife includes a lug, wherein the lug defines the longitudinal knife axis, wherein the lock is rotatable about the lug between the locked and unlocked configurations.

6. The apparatus of claim 5, wherein the lug is positioned at a lower end of the knife and projects distally.

7. The apparatus of claim 5, wherein the apparatus further comprises a spring configured to bias the lock towards the locked configuration, wherein the spring is positioned about the lug.

8. The apparatus of claim 1, the first jaw including a floor having an elongate slot extending along the longitudinal jaw axis and through which the knife is configured to translate, where a recess is formed in the floor and opens laterally to the elongate slot.

9. The apparatus of claim 1, wherein the lock includes a protrusion, wherein the first jaw includes a recess, wherein the protrusion is configured to be positioned inside of the recess and thus constrained longitudinally by the recess when the lock is in the locked configuration, wherein the protrusion is configured to be positioned outside of the recess and thus unconstrained longitudinally by the recess when the lock is in the unlocked configuration.

10. The apparatus of claim 1, wherein the lock includes a pin extending in a proximal direction towards the knife, wherein the pin is configured to engage a spring to thereby bias the lock towards the locked configuration.

11. The apparatus of claim 1, wherein the lock includes a protrusion, wherein the first jaw includes a recess, wherein the protrusion is configured to be positioned inside of the recess and thus constrained longitudinally by the recess when the lock is in the locked configuration, wherein the cam surface and the protrusion are circumferentially offset from one another.

12. The apparatus of claim 1, wherein the lock is longitudinally secured to the knife such that the lock is translatable longitudinally with the knife relative to the first and second jaws.

13. The apparatus of claim 1, wherein the knife is actuatable from a proximal home position to a distal fired position when the lock is in the unlocked configuration, wherein the lock is configured to automatically resume the locked configuration in response to the knife returning to the proximal home position from the distal fired position.

14. An apparatus comprising:
(a) a first jaw configured to selectively receive a staple cartridge and defining a longitudinal jaw axis;
(b) a second jaw, wherein the first and second jaws are configured to cooperate to clamp and staple tissue;
(c) a knife configured to actuate relative to the first jaw and the second jaw along the longitudinal jaw axis while the staple cartridge is housed within the first jaw to thereby cut and staple tissue clamped by the first and second jaws, wherein the knife defines a longitudinal knife axis that extends along the longitudinal jaw axis; and
(d) a lock configured to rotate about the longitudinal knife axis relative to the knife between an unlocked configuration and a locked configuration, wherein the lock is configured to inhibit distal actuation of the knife in the locked configuration and permit distal translation of the knife in the unlocked configuration, the lock including a collar and a spring positioned between the collar and the knife, wherein the spring is configured to bias the collar towards the locked configuration, wherein a portion of the collar extends within a portion of the spring.

15. The apparatus of claim 14, wherein the knife includes a lug, wherein the lug defines the longitudinal knife axis, wherein the lock is rotatable about the lug between the locked and unlocked configurations.

16. The apparatus of claim 14, wherein the lock includes a protrusion, wherein the first jaw includes a recess, wherein the protrusion is configured to be positioned inside of the recess and thus constrained longitudinally by the recess when the lock is in the locked configuration, wherein the protrusion is configured to be positioned outside of the recess and thus unconstrained longitudinally by the recess when the lock is in the unlocked configuration.

17. An apparatus comprising:
(a) a staple cartridge; and
(b) an end effector operable to clamp, staple, and cut tissue, comprising:
(i) a first jaw configured to selectively receive the staple cartridge,
(ii) a second jaw, wherein the first jaw and the second jaw are configured to transition between an open position and a closed position to clamp tissue, (iii) a knife configured to actuate distally relative to the first jaw and the second jaw along a firing stroke while the staple cartridge is housed within the first jaw to thereby cut and staple tissue clamped by the first and second jaws, the knife including a lug protruding longitudinally in a distal direction, and (iv) a lock annularly surrounding the lug and configured to rotate about the lug of the knife between an unlocked configuration and a locked configuration, wherein the lock is configured to inhibit distal actuation of the knife in the locked configuration and permit distal translation of the knife in the unlocked configuration, wherein the lock is configured to engage the staple cartridge to thereby rotate about the lug and to thus transition from the locked configuration to the unlocked configuration.

18. The apparatus of claim 17, wherein the staple cartridge includes a sled configured to directly contact and thereby drive the lock from the locked configuration to the unlocked configuration when the staple cartridge in an unspent state is fully seated within the first jaw.

19. The apparatus of claim 17, wherein the knife includes a distal-end surface, wherein the lug extends distally from the distal-end surface.

* * * * *